(12) United States Patent
Okamura

(10) Patent No.: US 9,562,863 B2
(45) Date of Patent: Feb. 7, 2017

(54) METHOD FOR DETERMINING LAYER DIRECTION OF CONDUCTOR LAYERS IN A MULTILAYER ELECTRONIC COMPONENT

(71) Applicant: MURATA MANUFACTURING CO., LTD., Kyoto (JP)

(72) Inventor: Kouki Okamura, Kyoto (JP)

(73) Assignee: Murata Manufacturing Co., Ltd., Kyoto-fu (JP)

( * ) Notice: Subject to any disclaimer, the term of this patent is extended or adjusted under 35 U.S.C. 154(b) by 352 days.

(21) Appl. No.: 14/145,211

(22) Filed: Dec. 31, 2013

(65) Prior Publication Data

US 2014/0109389 A1   Apr. 24, 2014

Related U.S. Application Data

(63) Continuation of application No. PCT/JP2012/067366, filed on Jul. 6, 2012.

(30) Foreign Application Priority Data

Jul. 6, 2011   (JP) .................. 2011-149735

(51) Int. Cl.
*G01N 21/84* (2006.01)
*B65G 15/04* (2006.01)
*G01N 29/24* (2006.01)
*B65B 15/04* (2006.01)
*H05K 13/02* (2006.01)
(Continued)

(52) U.S. Cl.
CPC .............. *G01N 21/84* (2013.01); *B65B 15/04* (2013.01); *G01J 5/10* (2013.01); *G01N 29/24* (2013.01); *G01N 29/2418* (2013.01); *H05K 13/022* (2013.01); *H05K 13/08* (2013.01); *C23C 28/322* (2013.01); *C23C 28/34* (2013.01); *Y10T 29/49004* (2015.01); *Y10T 29/53022* (2015.01)

(58) Field of Classification Search
CPC .... G01N 21/84; G01N 29/24; G01N 29/2418; B65B 15/04; G01J 5/10; C23C 28/322; C23C 28/34; H05K 13/022; H05K 13/08; Y10T 29/49004; Y10T 29/53022
See application file for complete search history.

(56) References Cited

U.S. PATENT DOCUMENTS 4,338,822 A * 7/1982 Yamaguchi ........ G01N 29/2418
                                                        73/643
5,608,166 A * 3/1997 Monchalin ......... G01N 29/2418
                                                        73/655
(Continued)

FOREIGN PATENT DOCUMENTS

CN    101276687 A    10/2008
JP    04133368 A *   5/1992
(Continued)

OTHER PUBLICATIONS

Machine Translation of Japanese Patent Publication JP 2005-17135, Mar. 2016.*

(Continued)

*Primary Examiner* — A. Dexter Tugbang
(74) *Attorney, Agent, or Firm* — Studebaker & Brackett PC

(57) ABSTRACT

A layer direction determining method for a multilayer electronic component to accurately determine the layer direction of conductor layers in the multilayer electronic component.

12 Claims, 12 Drawing Sheets

(51) Int. Cl.
  *H05K 13/08*  (2006.01)
  *G01J 5/10*  (2006.01)
  *C23C 28/00*  (2006.01)

(56) References Cited

U.S. PATENT DOCUMENTS

2008/0187776 A1\* 8/2008 Nakahara ............... C23C 28/322
                       428/656
2008/0239617 A1 10/2008 Motoki et al.
2011/0162180 A1  7/2011 Motoki et al.

FOREIGN PATENT DOCUMENTS

| | | |
|---|---|---|
| JP | 06-204075 A | 7/1994 |
| JP | 2001-319840 A | 11/2001 |
| JP | 2002-332113 A | 11/2002 |
| JP | 2005-017135 A | 1/2005 |
| JP | 2005-108801 A | 4/2005 |
| JP | 2005-164428 A | 6/2005 |
| JP | 2009-123897 A | 6/2009 |

OTHER PUBLICATIONS

International Search Report; PCT/JP2012/067366; Aug. 7, 2012.
Written Opinion of the International Searching Authorityl; PCT/JP2012/067366; Aug. 7, 2012.
F.Ogawa, "Shutterless movement of far-infrared camera and measurement of small temperature difference", Eizojoho industrial, Sep. 2010, pp. 61-65.

\* cited by examiner

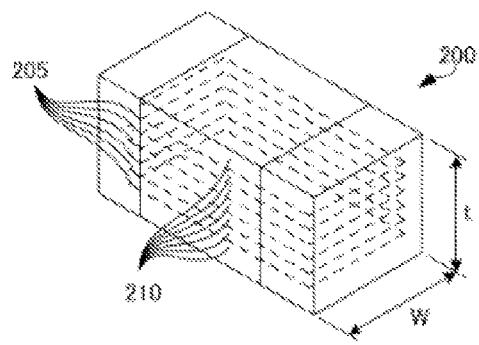
FIG. 1A
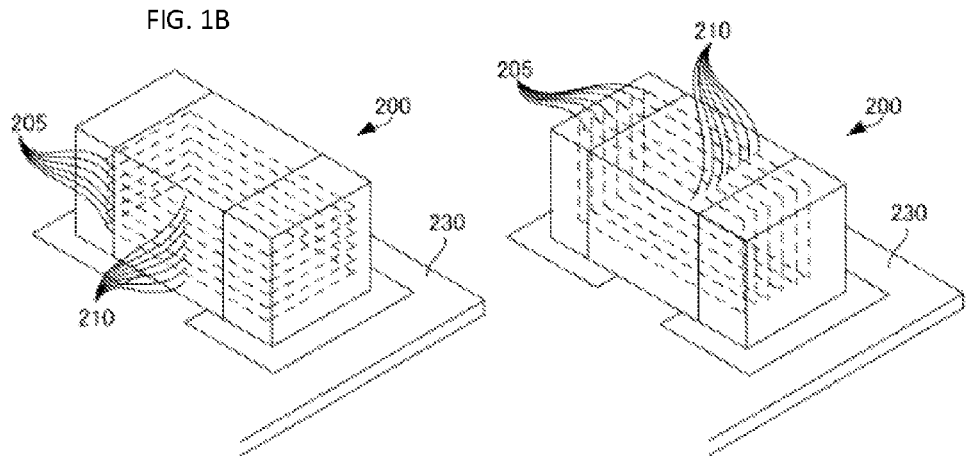
FIG. 1B
FIG. 1C

METHOD FOR DETERMINING LAYER DIRECTION OF CONDUCTOR LAYERS IN A MULTILAYER ELECTRONIC COMPONENT

CROSS REFERENCE TO RELATED APPLICATIONS

This application claims benefit of priority to Japanese Application No. 2011-149735 filed on Jul. 6, 2011, and to International Patent Application No. PCT/JP2012/067366 filed on Jul. 6, 2012, the entire content of each of which is incorporated herein by reference.

TECHNICAL FIELD

The present technical field relates to a layer direction determining method and layer direction determining apparatus of determining the layer direction of conductor layers layered in a multilayer electronic component, and a method and apparatus of manufacturing a series of multilayer electronic components to align the layer direction of the conductor layers in the multilayer electronic components with a certain direction.

BACKGROUND

Some electronic components, such as light emitting diodes (LEDs), have polarities. The polarities of such electronic components are required to be aligned in a certain direction for inspection or mounting of the electronic components.

In order to solve the above challenge, a disclosure of an alignment apparatus for electronic components has been hitherto disclosed (refer to Japanese Unexamined Patent Application Publication No. 2002-332113). This alignment apparatus takes pictures of the appearances of electronic components that move along a conveying path from a container with a camera to determine the polarity directions of the electronic components on the basis of polarity display, which represents an appearance feature. The alignment apparatus excludes the electronic components having polarity directions different from a certain direction from the conveying path and returns the electronic components in the container to align the polarities of the electronic components in the certain direction.

SUMMARY

Technical Problem

As illustrated in FIG. 1(A), a multilayer ceramic capacitor, which is a multilayer electronic component, has no polarity and has a configuration in which inner electrodes 205, which are conductor layers, and ceramic dielectrics 210, which are non-conductor layers, are alternately layered. Since a multilayer ceramic capacitor 200 has the above configuration, for example, the bending tolerance and/or the stress tolerance due to shrinkage of solder are varied depending on the mounting direction in which the multilayer ceramic capacitor 200 is mounted on a printed circuit board. Specifically, as illustrated in FIG. 1(B) and FIG. 1(C), when the multilayer ceramic capacitors 200 are mounted on a printed circuit board 230 without aligning the layer direction of the conductor layers in the multilayer ceramic capacitors 200 in a certain direction, the product is varied in quality. Since this problem generally occurs in the multilayer electronic components, it is necessary to determine the layer directions of the conductor layers in the multilayer electronic components before the components are mounted in order to stabilize the quality of the product.

However, with the alignment apparatus described in Japanese Unexamined Patent Application Publication No. 2002-332113, it is not possible to determine the layer direction of the conductor layers layered in the multilayer electronic component that does not have a distinctive appearance feature. For example, in the case of the rectangular parallelepiped multilayer ceramic capacitor 200 illustrated in FIG. 1(A), it is not possible to determine the layer direction of the conductor layers from the appearance when the difference between its height t and its width W is small.

It is an object of the present disclosure to provide a layer direction determining method and layer direction determining apparatus for a multilayer electronic component to accurately determine the layer direction of conductor layers in the multilayer electronic component, and a method and apparatus of manufacturing a series of multilayer electronic components to align the layer directions of the conductor layers in the multilayer electronic components in a certain direction.

Solution to Problem (1) A layer direction determining method for a multilayer electronic component of the present disclosure includes a measuring process and a determining process. A measured value concerning an amount of infrared energy detected from an area including an observation face where a multilayer electronic component in which conductor layers and non-conductor layers are layered is observed is acquired under a measurement condition that is set in advance in the measuring process. A threshold value corresponding to the measurement condition is set and the threshold value is compared with the measured value to determine a layer direction of the conductor layers in the multilayer electronic component on the basis of the result of the comparison in the determining process.

The multilayer electronic component is characterized in that the amounts of infrared energy detected from its outer faces are varied depending on the measurement conditions including the presence of heating, the heating direction, and the heating temperature and the layer direction of the conductor layers. For example, when the multilayer electronic component is not heated, the measured value concerning the amount of infrared energy detected from the observation face parallel to the conductor layers is higher than that detected from the observation face perpendicular to the conductor layers. When the lower face of the multilayer electronic component is heated at, for example, 50° C. and the upper face is used as the observation face, the measured value concerning the amount of infrared energy detected from the observation face parallel to the conductor layers is lower than that detected from the observation face perpendicular to the conductor layers. The use of such characteristics allows the layer direction of the conductor layers in the multilayer electronic component to be accurately determined.

(2) In (1), the measured value concerning the amount of infrared energy detected from the area including the observation face is a difference between detected values detected from a first area on the observation face and a second area different from the first area.

In the multilayer electronic component, the measured value concerning the amount of infrared energy detected from the face parallel to the conductor layers is different from that detected from the face perpendicular to the conductor layers depending on the measurement condition, as described above. Since the multilayer electronic component has the above characteristics, it is possible to accurately determine the layer direction of the conductor layers in the multilayer electronic component by calculating the difference between the detected value detected from the first area on the observation face and the detected value detected from the second area different from the first area and comparing the difference with the threshold value that is set in advance.

(3) In (2), the first area is one of two adjacent faces with a longitudinal side of the multilayer electronic component having a rectangular parallelepiped shape sandwiched therebetween, and the second area is the other of the two adjacent faces with the longitudinal side of the multilayer electronic component having the rectangular parallelepiped shape sandwiched therebetween.

In the above configuration, the two adjacent faces with the longitudinal side of the multilayer electronic component having the rectangular parallelepiped shape sandwiched therebetween is the face parallel to the conductor layers and the face perpendicular to the conductor layers. Since the two faces differs from each other in the layer direction of the conductor layers, the measured values concerning the amounts of infrared energy detected from the respective faces are different from each other depending on the measurement condition. Accordingly, it is possible to accurately determine the layer direction of the conductor layers in the multilayer electronic component by calculating the difference between the detected values from the respective faces and comparing the calculated difference with the threshold value set in accordance with the measured values.

(4) In (2), the first area is an area excluding an outer electrode of the multilayer electronic component, and the second area is an area other than the multilayer electronic component.

When the multilayer electronic component or a conveying block is varied in temperature, the layer direction of the conductor layers in the multilayer electronic component may not be accurately determined with the threshold value that is initially set. In such a case, since the temperature of a member around the multilayer electronic component, which is not the multilayer electronic component, is also varied as in the multilayer electronic component, the variation in temperature of the member around the multilayer electronic component is used to perform the measurement. Specifically, the difference between the measured value concerning the amount of infrared energy in the area excluding the outer electrode of the multilayer electronic component and the measured value concerning the amount of infrared energy acquired in the area other than the multilayer electronic component is calculated. For example, in a mass production line, an image of a rotary circular plate which is concurrently captured with the camera is set to the second area and the amount of infrared energy in the first area of the multilayer electronic component is acquired as a relative value by using the amount of infrared energy in the second area as a reference value. Since the effect of the variation in temperature on the multilayer electronic component or the conveying block can be cancelled in the above manner, it is possible to accurately determine the layer direction of the conductor layers in the multilayer electronic component.

(5) In (2), the first area is an area where the amount of infrared energy is varied depending on an orientation of the multilayer electronic component, and the second area is an area on the multilayer electronic component, where the amount of infrared energy is not varied regardless of the orientation of the multilayer electronic component.

In the above configuration, the relative value of the amount of infrared energy is acquired by using the measured value concerning the amount of infrared energy acquired in the second area as the reference value. For example, since the amount of infrared energy is not varied regardless of the orientation of the multilayer electronic component on, for example, the outer electrode or an area in a side margin, the relative value of the amount of infrared energy is acquired by using the measured value concerning the amount of infrared energy acquired in this area as the reference value to cancel the effect of the variation in temperature on the multilayer electronic component or the conveying block. Accordingly, it is possible to accurately determine the layer direction of the conductor layers in the multilayer electronic component.

(6) In any of (1) to (5), the measurement condition that is set in advance to acquire the measured value concerning the amount of infrared energy includes at least one of the presence of heating of the multilayer electronic component, a heating direction, and a heating temperature.

The use of the measured value concerning the amount of infrared energy detected from the area including the observation face where the multilayer electronic component is observed and the change of the threshold value in accordance with the measurement condition that is set in advance allow the layer direction of the conductor layers to be determined. For example, when the multilayer electronic component is not heated, the measured value concerning the amount of infrared energy detected from the face parallel to the conductor layers is higher than that detected from the face perpendicular to the conductor layers. When the upper face of the multilayer electronic component is set as the observation face and the lower face (bottom face) of the multilayer electronic component is heated, for example, at 50° C., the measured value concerning the amount of infrared energy detected from the face perpendicular to the conductor layers is higher than that detected from the face parallel to the conductor layers. When the upper face of the multilayer electronic component is set as the observation face and the upper face of the multilayer electronic component is heated, the measured value concerning the amount of infrared energy detected from the face parallel to the conductor layers is higher than that detected from the face perpendicular to the conductor layers. As described above, the measured value concerning the amount of infrared energy detected from the face parallel to the conductor layers is different from that detected from the face perpendicular to the conductor layers depending on the measurement condition that is set in advance. Accordingly, the change of the threshold value in accordance with the measurement condition allows the layer direction of the conductor layers in the multilayer electronic component to be more accurately determined.

(7) In any of (1) to (6), the threshold value is set on the basis of a measured value concerning an amount of infrared energy detected from an observation face of a reference multilayer electronic component the shape and the characteristics of which are the same as those of a multilayer electronic component to be measured and the layer direction of the conductor layers in which is known if the reference multilayer electronic component is measured under the measurement condition.

In the above configuration, the reference multilayer electronic component, the layer direction of the conductor layers in which is known, can be used to set the threshold value of the measured value concerning the amount of infrared energy detected from the observation face without processing. It is possible to accurately determine whether the observation face is the face parallel to the conductor layers or the face perpendicular to the conductor layers by comparing the threshold value with the measured value.

(8) In any of (1) to (7), the multilayer electronic component in the measuring process is preferably in a state in which the temperature is higher than normal temperature.

The heating of the multilayer electronic component increases the amounts of infrared energy detected from the respective faces of the multilayer electronic component to increase the measured values themselves concerning the amounts of infrared energy detected from the face parallel to the conductor layers in the multilayer electronic component and the face perpendicular to the conductor layers in the multilayer electronic component, thus increasing the difference between the measured values depending on the measurement condition. Accordingly, it is possible to easily determine the layer direction of the conductor layers in the multilayer electronic component.

(9) The measuring process includes a capturing step and a step of acquiring the measured value concerning the amount of infrared energy detected from the observation face. In the capturing step, a thermal image on the observation face of the multilayer electronic component is captured. In the step of acquiring the measured value concerning the amount of infrared energy detected from the observation face, the measured value concerning the amount of infrared energy detected from the observation face of the multilayer electronic component is acquired on the basis of the thermal image captured in the capturing step.

The capture of the thermal image on the observation face of the multilayer electronic component allows an image corresponding to the amount of infrared energy detected from the observation face to be acquired. Accordingly, for example, a process of averaging the amount of infrared energy detected from the observation face can be performed to allow the layer direction of the conductor layers in the multilayer electronic component to be accurately determined even if the amount of infrared energy is slightly varied.

(10) In the layer direction determining method for a multilayer electronic component of the present disclosure, a temperature is used as the measured value concerning the amount of infrared energy detected from the observation face of the multilayer electronic component. The temperature on the observation face is easily measured by using, for example, an infrared camera or a radiation thermometer. Accordingly, it is possible to easily determine the layer direction of the conductor layers in the multilayer electronic component.

(11) A layer direction determining apparatus for a multilayer electronic component of the present disclosure includes measuring means and determining means. The measuring means acquires a measured value concerning an amount of infrared energy detected from an observation face where a multilayer electronic component in which conductor layers and non-conductor layers are layered is observed. The determining means sets a threshold value corresponding to a measurement condition and compares the threshold value with the measured value to determine a layer direction of the conductor layers in the multilayer electronic component on the basis of the result of the comparison.

With the layer direction determining apparatus for a multilayer electronic component, it is possible to accurately determine the layer direction of the conductor layers in the multilayer electronic component on the basis of the measured value concerning the amount of infrared energy detected from the observation face.

(12) In (11), the measured value concerning the amount of infrared energy detected from the area including the observation face is the difference between detected values detected from a first area on the observation face and a second area different from the first area.

In the multilayer electronic component, the measured value concerning the amount of infrared energy detected from the face parallel to the conductor layers is different from that detected from the face perpendicular to the conductor layers depending on the measurement condition. The layer direction determining apparatus for a multilayer electronic component calculates the difference between the detected value from the first area on the observation face and the detected value from the second area on the basis of the above characteristics to compare the difference with the threshold value that is set in advance. Accordingly, it is possible to accurately determine the layer direction of the conductor layers in the multilayer electronic component depending on the measurement condition.

(13) In (12), the first area is one of two adjacent faces with a longitudinal side of the multilayer electronic component having a rectangular parallelepiped shape sandwiched therebetween, and the second area is the other of the two adjacent faces with the longitudinal side of the multilayer electronic component having the rectangular parallelepiped shape sandwiched therebetween.

Since the face parallel to the conductor layers and the face perpendicular to the conductor layers, which are the two adjacent faces of the multilayer electronic component, are different from each other in the layer direction of the conductor layers, the measured value concerning the amount of infrared energy detected from the face parallel to the conductor layers is different from that detected from the face perpendicular to the conductor layer depending on the measurement condition. With the layer direction determining apparatus for a multilayer electronic component, it is possible to accurately determine the layer direction of the conductor layers in the multilayer electronic component by calculating the difference between the detected values from the two faces on the basis of the above characteristics to compare the difference with the threshold value set in accordance with the measured values.

(14) In (12), the first area is an area excluding an outer electrode of the multilayer electronic component, and the second area is an area other than the multilayer electronic component.

When the multilayer electronic component or the conveying block is greatly varied in temperature due to, for example, the variation in ambient temperature, the layer direction of the conductor layers in the multilayer electronic component may not be accurately determined with the threshold value that is initially set. In such a case, since the temperature of a member around the multilayer electronic component, which is not the multilayer electronic component, is also varied as in the multilayer electronic component, the variation in temperature of the member around the multilayer electronic component is used to perform the measurement. Specifically, the difference between the measured value concerning the amount of infrared energy in the area excluding the outer electrode of the multilayer electronic component and the measured value concerning the amount of infrared energy acquired in the area other than the multilayer electronic component is calculated. For example, in the mass production line, an image of the rotary circular plate which is concurrently captured with the camera is set to the second area and the amount of infrared energy in the first area of the multilayer electronic component is acquired as a relative value by using the amount of infrared energy in the second area as a reference value. Since the effect of the variation in temperature on the multilayer electronic component or the conveying block can be cancelled in the above manner, it is possible to accurately determine the layer direction of the conductor layers in the multilayer electronic component with the layer direction determining apparatus for a multilayer electronic component.

(15) In (12), the first area is an area where the amount of infrared energy is varied depending on an orientation of the multilayer electronic component, and the second area is an area on the multilayer electronic component, where the amount of infrared energy is not varied regardless of the orientation of the multilayer electronic component.

In the above configuration, the relative value of the amount of infrared energy is acquired by using the measured value concerning the amount of infrared energy acquired in the second area as the reference value. For example, the amount of infrared energy is not varied regardless of the orientation of the multilayer electronic component on, for example, the outer electrode or an area in a side margin. Since the layer direction determining apparatus for a multilayer electronic component acquires the relative value of the amount of infrared energy by using the measured value concerning the amount of infrared energy acquired in this area as the reference value, the effect of the variation in temperature on the multilayer electronic component or the conveying block can be cancelled. Accordingly, it is possible to accurately determine the layer direction of the conductor layers in the multilayer electronic component.

(16) In any of (11) to (15), the layer direction determining apparatus for a multilayer electronic component further includes conveying means for conveying the multilayer electronic component. The measuring means measures the measured value concerning the amount of infrared energy detected from the area including the observation face of the multilayer electronic component that is being conveyed via a cover member through which an infrared ray is transmitted.

Even if the multilayer electronic component that is being conveyed jumps up or drops due to vibration or the like while the amounts of infrared energy detected from the faces of the multilayer electronic component are being measured, the cover member prevents the multilayer electronic component from being broken due to the jumping or the dropping. Accordingly, it is possible to prevent the measuring means of the amount of infrared energy from being broken.

(17) In (16), the cover member is spaced from the multilayer electronic component that is being conveyed.

If the cover member comes into contact with the multilayer electronic component, heat conduction is dominant over radiation in heat propagation and it is difficult to measure the measured value concerning the amount of infrared energy detected from the multilayer electronic component. However, it is possible to measure the measured value concerning the amount of infrared energy detected from each face of the multilayer electronic component with no problem by measuring the measured value concerning the amount of infrared energy via the cover member that is not in contact with the multilayer electronic component.

(18) In (16) or (17), the cover member has a protective surface film formed on its face opposing the multilayer electronic component.

Since the protective surface film is formed on the face of the cover member, which opposes the multilayer electronic component, it is possible to prevent the cover member from being scratched or worn even if the multilayer electronic component jumps up due to the vibration during the conveyance of the multilayer electronic component to abut against the cover member.

(19) In any of (11) to (18), the layer direction determining apparatus for a multilayer electronic component further includes conveying means for conveying the multilayer electronic component. The measuring means acquires the measured value concerning the amount of infrared energy detected from the observation face of the multilayer electronic component that is being conveyed via a cover member in which a through hole smaller than the width of the multilayer electronic component is formed.

Since the cover member has the through hole formed therein, the amount of infrared energy can be measured via the through hole even if the cover member is damaged to make the measurement of the amounts of infrared energy detected from the faces of the multilayer electronic component difficult. Since the amount of infrared energy can be measured via the through hole, the cover member can be made of a material through which the infrared rays are not transmitted to reduce the cost by using an inexpensive material. Since the through hole is smaller than the width of the multilayer electronic component, the multilayer electronic component is inhibited from being fitted into the through hole.

(20) A method of manufacturing a series of multilayer electronic components housed in a base material including multiple housings of the present disclosure includes a sorting process and a housing process. Multiple multilayer electronic components the conductor layers in which are determined to have a certain layer direction by the layer direction determining method for a multilayer electronic component described in any of (1) to (10) are sorted in the sorting process. The multiple multilayer electronic components sorted in the sorting process are housed in the multiple housings in a state in which the conductor layers are aligned with the certain layer direction in the housing process.

In the above configuration, the multiple multilayer electronic components the conductor layers in which are determined to have the certain layer direction are housed in the base material including the multiple housings in the state in which the layer directions of the conductor layers are aligned with the certain layer direction. Accordingly, the use of the multilayer electronic component housed in the series of multilayer electronic components allows the layer directions of the conductor layers to be aligned when the multilayer electronic components are mounted. Accordingly, it is possible to stabilize the quality of the product in which the multilayer electronic components are mounted.

(21) In (20), the method of manufacturing a series of multilayer electronic components further includes a process of changing an orientation of the multilayer electronic component so that the layer direction of the conductor layers is aligned with the certain direction if the layer direction of the conductor layers determined in the determining method is different from the certain direction.

The use of the result of the determination of the layer directions of the conductor layers in the multilayer electronic components allows the orientations of the multilayer electronic components to be unified so that the layer direction of the conductor layers is aligned with the certain direction. Accordingly, the reliability of the result of detection of the multilayer electronic component is improved. In addition, it is possible to unify the characteristics of the product in which the multilayer electronic components are mounted.

(22) An apparatus of manufacturing a series of multilayer electronic components housed in a base material including multiple housings of the present disclosure includes sorting means and heating means. The sorting means sorts multiple multilayer electronic components the conductor layers in which are determined to have a certain layer direction by the layer direction determining apparatus for a multilayer electronic component described in any of (11) to (19). The housing means houses the multiple multilayer electronic components sorted by the sorting means in the multiple housings in a state in which the layer directions of the conductor layers are aligned with the certain layer direction.

In the above configuration, the multiple multilayer electronic components the conductor layers in which are determined to have the certain layer direction are housed in the base material including the multiple housings in the state in which the layer directions of the conductor layers are aligned with the certain layer direction. Accordingly, the use of the series of multilayer electronic components manufactured by the apparatus of manufacturing a series of multilayer electronic components allows the layer directions of the conductor layers to be aligned when the multilayer electronic components are mounted. As a result, it is possible to stabilize the quality of the product in which the multilayer electronic components are mounted.

(23) In (22), the apparatus of manufacturing a series of multilayer electronic components further includes direction changing means. The direction changing means changes an orientation of the multilayer electronic component so that the layer direction is aligned with the certain layer direction if the layer direction of the conductor layers determined by the determining apparatus is different from the certain layer direction.

In the above configuration, the direction changing means can be used to unify the orientations of the multilayer electronic components so that the layer directions of the conductor layers are aligned with the certain direction. Accordingly, the use of the series of multilayer electronic components manufactured by the apparatus of manufacturing a series of multilayer electronic components allows the characteristics of the product in which the multilayer electronic components are mounted to be unified.

Advantageous Effects of Disclosure

According to the present disclosure, it is possible to accurately determine the layer direction of the conductor layers in the multilayer electronic component. In addition, it is possible to manufacture the series of multilayer electronic components, the layer directions of the conductor layers of which are aligned in a certain direction.

BRIEF DESCRIPTION OF THE DRAWINGS

FIG. 1(A) is an oblique perspective view illustrating the configuration of a multilayer ceramic capacitor, FIG. 1(B) is an oblique perspective view representing a case in which conductor layers in the multilayer ceramic capacitor are mounted so as to oppose a printed circuit board, and FIG. 1(C) is an oblique perspective view representing a case in which the conductor layers in the multilayer ceramic capacitor are mounted so as to be orthogonal to the printed circuit board.

FIG. 3(A) illustrates a state in which the amounts of infrared energy of the two multilayer capacitors are measured when a heater at a bottom face side is turned off and FIG. 3(B) illustrates a state in which the amounts of infrared energy of the two multilayer capacitors are measured when the heater at the lower face side is turned on.

DETAILED DESCRIPTION

Multilayer Electronic Component

Multilayer electronic components will now be described. The multilayer electronic components each have a configuration in which inner electrode layers, dielectric layers, and magnetic layers, which are inner layers, are layered. The multilayer electronic components include multilayer ceramic capacitors, multilayer coils, multilayer thermistors, and multilayer piezoelectric bodies. The inner electrode layers are conductor layers, and the dielectric layers and the magnetic layers are non-conductor layers made of materials different from the material of the inner electrodes. In the present disclosure, determination of the layer directions of the conductor layers (hereinafter simply referred to as layer directions) and alignment of the layer directions are performed for finished products of the multilayer electronic components and semifinished products of the multilayer electronic components before burning. A case will be described below in which the determination of the layer direction and change of the layer direction are performed for the multilayer ceramic capacitor. The multilayer ceramic capacitor is simply referred to as a multilayer capacitor in the following description.

Figure 2A:
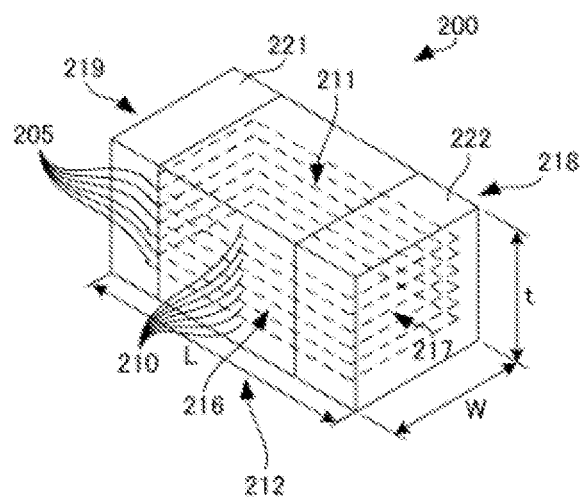
FIG. 2(A) is an oblique perspective view illustrating the configuration of a multilayer ceramic capacitor.
Figure 2B:
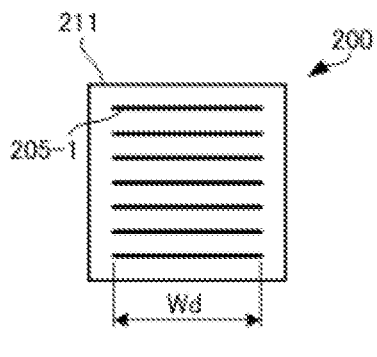
FIG. 2(B) is a cross-sectional view of a multilayer capacitor in which an upper face side is parallel to the conductor layers.
Figure 2C:
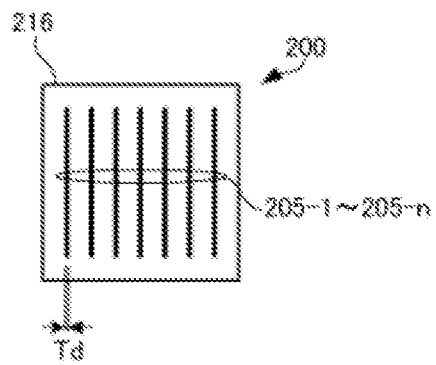
FIG. 2(C) is a cross-sectional view of a multilayer capacitor in which the upper face side is perpendicular to the conductor layers.

FIG. 2(A) is an oblique perspective view illustrating the configuration of a multilayer ceramic capacitor. FIG. 2(B) is a cross-sectional view of a multilayer capacitor in which the upper face side is parallel to the conductor layers. FIG. 2(C) is a cross-sectional view of a multilayer capacitor in which the upper face side is perpendicular to the conductor layers.

As illustrated in FIG. 2(A), a multilayer capacitor 200 has a rectangular parallelepiped shape and has a configuration in which planar conductor layers 205 and non-conductor layers, which are ceramic dielectrics 210, are alternately layered. An upper face 211 and a lower face 212 parallel to the multiple conductor layers 205 are referred to as parallel faces 211 and 212. Side faces 216 to 219 which are perpendicular to the multiple conductor layers 205 and on which the end portions of the multiple conductor layers 205 are arranged are referred to as perpendicular faces 216 to 219. A first outer electrode 221 and a second outer electrode 222 are formed on the perpendicular face 217 and the perpendicular face 219 in the longitudinal direction of the ceramic dielectrics 210. The first outer electrode 221 and the second outer electrode 222 are connected to multiple (n-number) conductor layers 205-1 to 205-n. The conductor layers 205-1 to 205-n are layered at certain intervals. As illustrated in FIG. 2(B) and FIG. 2(C), the conductor layers 205-1 to 205-n each have a width Wd and a thickness Td.

The ceramic dielectrics 210 are made of barium titanate. The conductor layers 205 are made of nickel. The first outer electrode 221 and the second outer electrode 222 are metal-plated.

The size (length (L)×width (W)×height (t)) of the multilayer capacitor 200 is, for example, 1.6 mm×0.8 mm×0.8 mm (1608) or 1.0 mm×0.5 mm×0.5 mm (1005).

Method of Determining Layer Direction of Multilayer Electronic Component

The inventor of the present application studied a new method of determining the layer direction of the conductor layers in the multilayer electronic component in a non-destructive manner. The inventor inferred that the layer direction of the conductor layers in the multilayer electronic component is capable of being determined by detecting the amount of infrared energy on an observation face of the multilayer capacitor (hereinafter sometimes referred to as a work). Accordingly, the inventor performed the following experiments in order to confirm which influencing factors exist.

First Experiment

The amounts of infrared energy on the observation faces of works were detected in a state in which no heating factor is externally applied. This state is illustrated in FIG. 3(A).

Figure 3A:
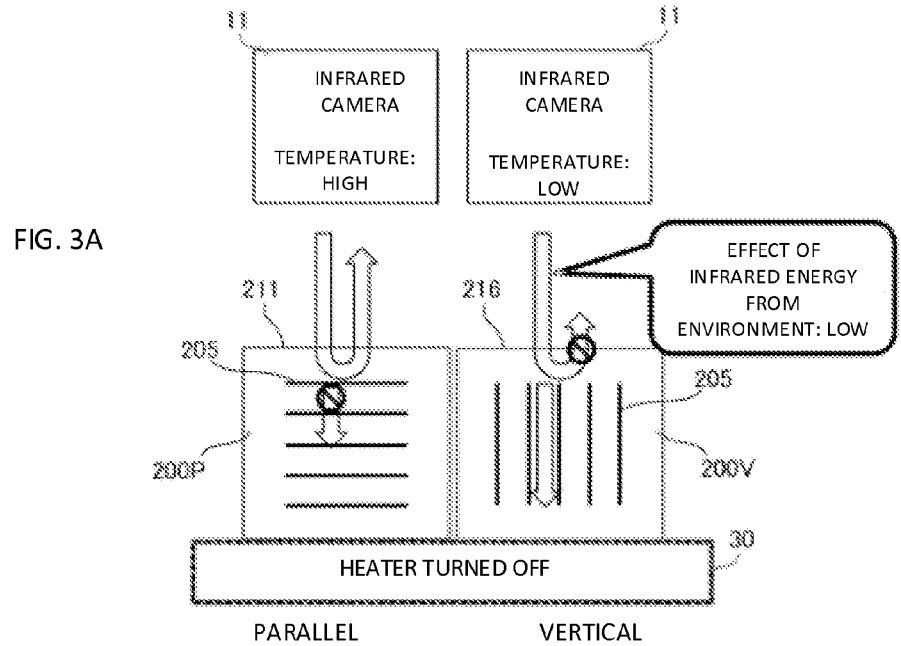

Referring to FIG. 3(A), a work 200P is oriented so that the parallel face 211 is used as the observation face. A work 200V is oriented so that the perpendicular face 216 is used as the observation face. The same applies to FIG. 3(B), FIG. 4(A), and FIG. 4(B) described below.

The first experiment was performed in the following manner.

1. Multiple works at normal temperature are placed on a heater 30 (its surface temperature is 25° C., which is the normal temperature) which is turned off. The multiple works are in a state in which the layer directions of the conductor layers 205 are varied, that is, in a state in which the multiple works include the work 200P and the work 200V.

2. The amounts of infrared energy detected from the observation faces (the upper faces) of the multiple works are measured with an infrared camera.

Second Experiment

Figure 3B:
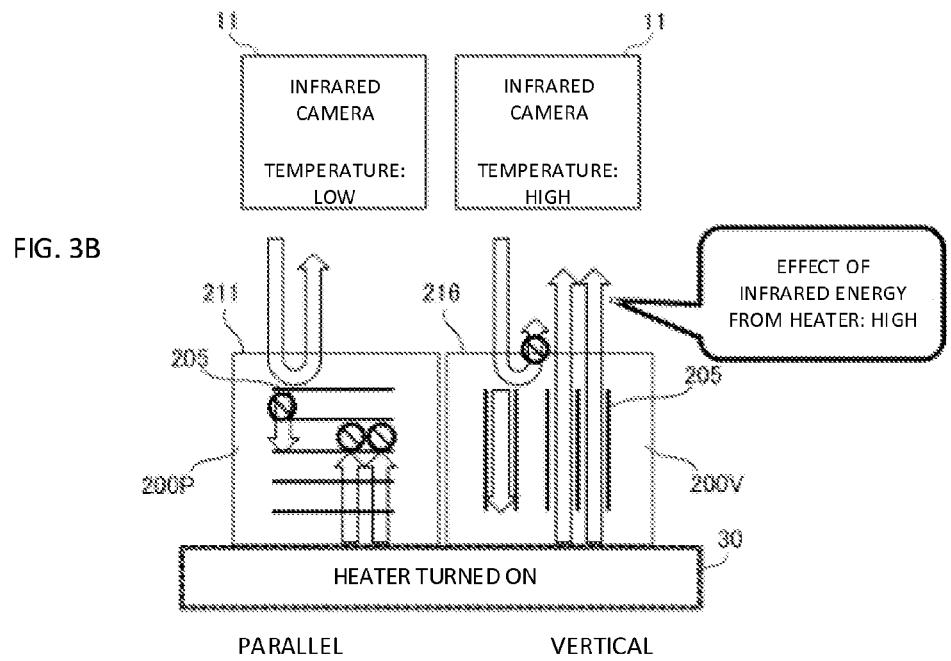

The amounts of infrared energy on the observation faces of works were detected in a state in which a heating factor is externally applied. However, the heating is performed with the heater 30 arranged under the lower faces of the works. This state is illustrated in FIG. 3(B).

The second experiment was performed in the following manner.

1. The surface temperature of the heater 30 is set to a value higher than the normal temperature (for example, 30° C.)

2. Multiple works at the normal temperature are placed on the heater 30 to directly heat the lower face of each work. The multiple works are in the state in which the layer directions of the conductor layers 205 are varied, that is, in the state in which the multiple works include the work 200P and the work 200V.

3. Immediately after the multiple works are placed on the heater 30, the amounts of infrared energy detected from the observation faces (the upper faces) are measured with the infrared camera.

4. The multiple works are shifted from the heater 30.

5. The temperature of the heater 30 is increased by a certain value (for example, 5° C.)

6. The above steps 2 to 5 are repeated until the surface temperature of the heater 30 is increased to 100° C.

Third Experiment

Figure 4A:
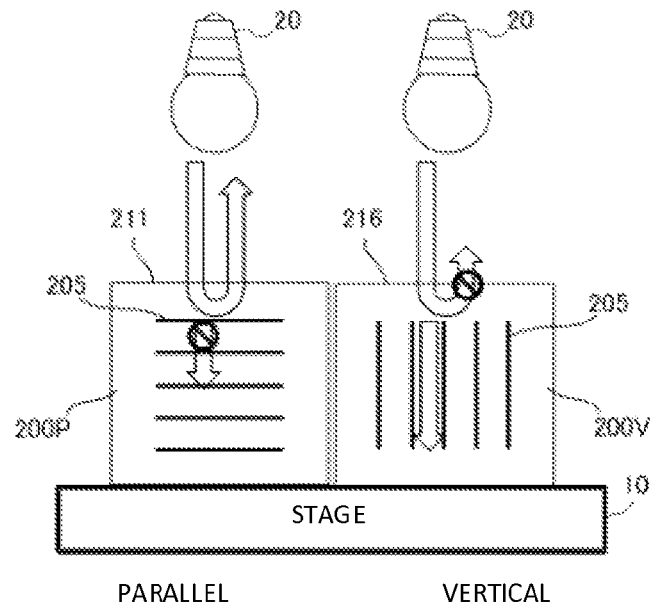
FIG. 4(A) illustrates a state in which an observation face of the multilayer capacitor is heated with a lamp at the upper face side turned on and FIG. 4(B) illustrates a state in which the amounts of infrared energy of the multilayer capacitors are measured after the observation face is heated with the lamp at the upper face side.
Figure 4B:
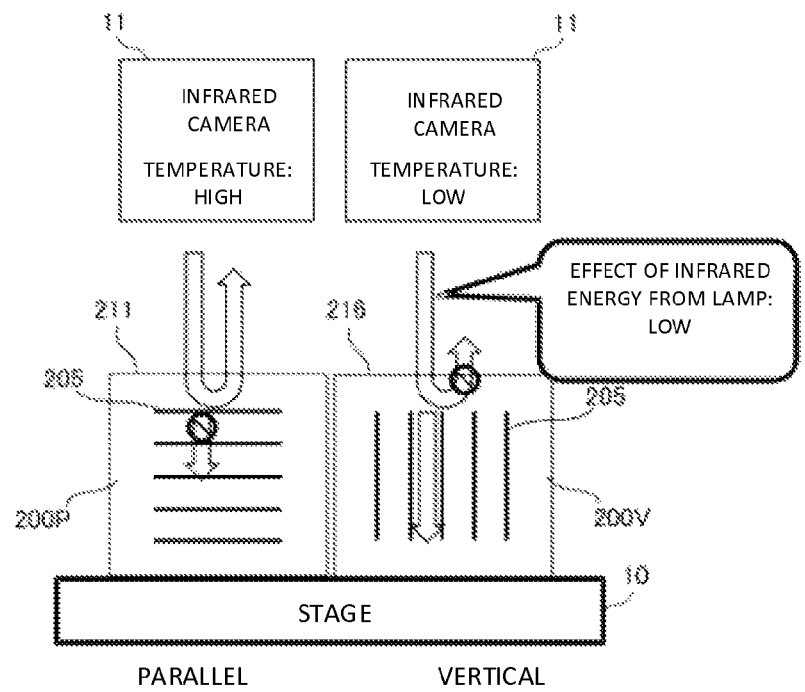

The amounts of infrared energy on the observation faces of works were detected in the state in which a heating factor is externally applied. However, the heating is performed with a lamp 20 arranged above the upper faces of the works. This state is illustrated in FIG. 4(A) and FIG. 4(B).

The third experiment was performed in the following manner.

1. Multiple works at the normal temperature are placed on a stage 10. The multiple works are in the state in which the layer directions of the conductor layers 205 are varied, that is, in the state in which the multiple works include the work 200P and the work 200V.

2. The lamp is arranged above the upper faces of the multiple works and the lamp is turned on for a certain period of time (for example, for several seconds) to indirectly heat the upper face of each work.

3. The lamp is turned off and is moved.

4. The amounts of infrared energy detected from the upper faces of the multiple works are measured with the infrared camera.

The above first to third experiments were performed for multiple works of different types.

Figure 5:
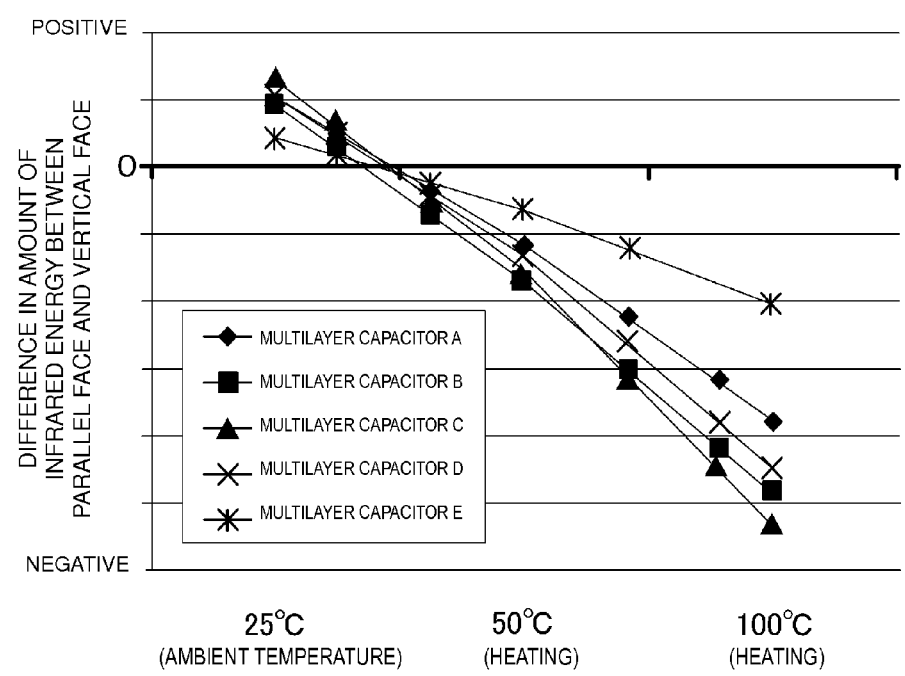
FIG. 5 is a graph illustrating the relationship of the difference in temperature between the multilayer capacitor the observation face of which is a parallel face and the multilayer capacitor the observation face of which is a perpendicular face.

FIG. 5 is a graph illustrating the results of the first and second experiments.

Result of First Experiment

When the works were not heated, the infrared energy detected from the work 200P was greater than that detected from the work 200V. In other words, (the amount of infrared energy on the parallel face)−
(the amount of infrared energy on the perpendicular face)>0

As illustrated in FIG. 5, the infrared energy detected from the multilayer capacitor was varied with the type of the multilayer capacitor.

Result of Second Experiment (A) When the lower faces of the works were heated, the amount of infrared energy detected from the work 200P was greater than that detected from the work 200V if the surface temperature of the heater 30 is lower than a specific temperature (35° C.) In other words, (the amount of infrared energy on the parallel face)−
(the amount of infrared energy on the perpendicular face)>0

(B) When the lower faces of the works were heated, the amount of infrared energy detected from the work 200P was equal to that detected from the work 200V if the surface temperature of the heater 30 is at the specific temperature. In other words, (the amount of infrared energy on the parallel face)−
(the amount of infrared energy on the perpendicular face)=0

(C) When the lower faces of the works were heated, the amount of infrared energy detected from the work 200P was smaller than that detected from the work 200V if the surface temperature of the heater 30 exceeds the specific temperature. In other words, (the amount of infrared energy on the parallel face)−
(the amount of infrared energy on the perpendicular face)<0

As described above, the difference in the amount of infrared energy between the parallel face and the perpendicular face takes a positive value or a negative value with respect to the specific temperature. This temperature is referred to as a boundary temperature.

As illustrated in FIG. 5, the infrared energy detected from the work was varied with the type of the multilayer capacitor. In addition, the boundary temperature was varied with the type of the multilayer capacitor.

Result of Third Experiment

When the upper faces of the works were heated, the same result as the one in the first experiment was achieved. Specifically, (the amount of infrared energy on the parallel face)−
(the amount of infrared energy on the perpendicular face)>0

The infrared energy detected from the work was varied with the type of the multilayer capacitor.

On the basis of the results of the first to third experiments, the inventor of the present application inferred about the amounts of infrared energy detected from the observation faces of the works as follows:

As illustrated in FIG. 3(A), FIG. 4(A), and FIG. 4(B), since the work 200P is prone to reflect the infrared energy radiated from the upper face side of the work owing to the faces of the conductor layers 205, the infrared energy is difficult to be transmitted to the lower face side of the work. Since the work 200V is difficult to reflect the infrared energy radiated from the upper face side of the work at the end portions of the conductor layer 205, the infrared energy radiated from the upper face side of the work is prone to be transmitted to the lower face side of the work owing to the non-conductor layers 210.

As illustrated in FIG. 3(B), since the work 200P is prone to reflect the infrared energy radiated from the lower face side of the work owing to the faces of the conductor layers 205, the infrared energy is difficult to be transmitted to the upper face side of the work. Since the work 200V is difficult to reflect the infrared energy radiated from the lower face side of the work at the end portions of the conductor layers 205, the infrared energy radiated from the lower face side of the work is prone to be transmitted to the upper face side of the work owing to the non-conductor layers 210.

The conductor layers 205 and the non-conductor layers 210 of the works behave in the above manner. Accordingly, when the works are not externally heated and when the works are heated from above the upper faces, an infrared camera 11 mainly detects the infrared energy radiated from the work itself and the infrared energy reflected from the conductor layers 205 in the case of the work 200P while the infrared camera 11 mainly detects the infrared energy radiated from the work itself in the case of the multilayer capacitor 200V. Consequently, the infrared energy detected from the work 200P is constantly higher than that detected from the work 200V when the works are not externally heated and when the works are heated from above the upper faces.

When the multilayer capacitors are heated from under the lower faces, the infrared camera 11 detects the infrared energy radiated from the work itself and the infrared energy radiated from the conductor layers 205 from the observation face in the case of the work 200P while the infrared camera 11 detects the infrared energy radiated from the work itself and the infrared energy transmitted through the non-conductor layers 210 from the observation face in the case of the multilayer capacitor 200V. In this case, in the multilayer capacitor 200V, the amount of infrared energy transmitted through the non-conductor layers 210 is varied with the surface temperature of the heater 30, that is, the amount of infrared energy radiated from the heater 30. Accordingly, when the works are heated from under the lower faces, the magnitude relationship between the infrared energy detected from the work 200P and the infrared energy detected from the work 200V is varied depending on the amount of infrared energy radiated from the heater that heats up the lower face of the work 200P.

As described above, the amount of infrared energy detected from the observation face of the multilayer capacitor 200 is varied with measurement conditions including the presence of external heating, the direction of the heating, and the heating temperature.

In the present disclosure, the measurement conditions are set in advance and a threshold value is set in accordance with the measurement conditions. Under the measurement conditions, the measurement values concerning the amounts of infrared energy detected from the outer periphery of the multilayer capacitor are measured. The threshold value set in accordance with the measurement conditions is compared with the measurement values concerning the amounts of infrared energy to determine and align the layer directions of the conductor layers in the multilayer capacitors on the basis of the result of the comparison. The measurement values concerning the amounts of infrared energy are not limited to the amount of infrared energy and the temperature and other values may be used as long as the use of the measurement values allows the layer direction of the conductor layers in the multilayer capacitor to be determined.

From the above results of the experiments, when the type of the multilayer capacitor 200 is varied, it is necessary to set the threshold value corresponding to the type, in addition to the above measurement conditions.

When the heater 30 is provided at the lower face side of the multilayer capacitor 200, the surface temperature of the heater 30 is preferably set to a temperature state that is higher than the normal temperature as much as possible and that is within a range in which the characteristics of the multilayer capacitor 200 are not affected. This causes the difference in the detected amount of infrared energy between when the observation face of the multilayer capacitor 200 is the parallel face 211 and when the observation face of the multilayer capacitor 200 is the perpendicular face 216 to be increased, as illustrated in FIG. 4, to allow the layer direction of the conductor layers 205 in the multilayer capacitor 200 to be reliably determined.

Since the amount of infrared energy detected from the parallel face of the multilayer capacitor is different from that detected from the perpendicular face of the multilayer capacitor, as described above, the inventor of the present application considered that the temperature displayed in a radiation thermometer may be varied and, thus, measured the surface temperature of the multilayer capacitor with the radiation thermometer. As a result, the inventor of the present application found that the surface temperature that is displayed is varied between the parallel face of the multilayer capacitor and the perpendicular face thereof. For example, in the measurement at a certain time, the surface temperature that was displayed for the parallel face of the multilayer capacitor was 30° C. while the surface temperature that was displayed for the perpendicular face of the multilayer capacitor was 28° C. Also in the measurements at other times, the surface temperatures that were displayed for the parallel face of the multilayer capacitor were higher than the surface temperatures that were displayed for the perpendicular face of the multilayer capacitor. Since the measurement value of the surface temperature with the radiation thermometer on the parallel face with respect to the conductor layers in the multilayer capacitor is different from that on the perpendicular face with respect to the conductor layers in the multilayer capacitor, it is also possible to determine the layer direction of the multilayer capacitor on the basis of the results of the measurement of the surface temperatures on the observation faces of the multilayer capacitor with the radiation thermometer.

When the surface temperatures on the observation faces of the multilayer capacitor were measured with a thermocouple, the surface temperature of the parallel face of the multilayer capacitor were the same as that of the perpendicular face of the multilayer capacitor. The difference in temperature occurs in the measurement of the surface temperatures on the observation faces with the radiation thermometer because the radiant energy of the infrared rays is varied depending on the observation face to vary the value resulting from temperature conversion of the infrared energy according to, for example, Stefan-Boltzmann's law.

First Embodiment

Figure 6A:
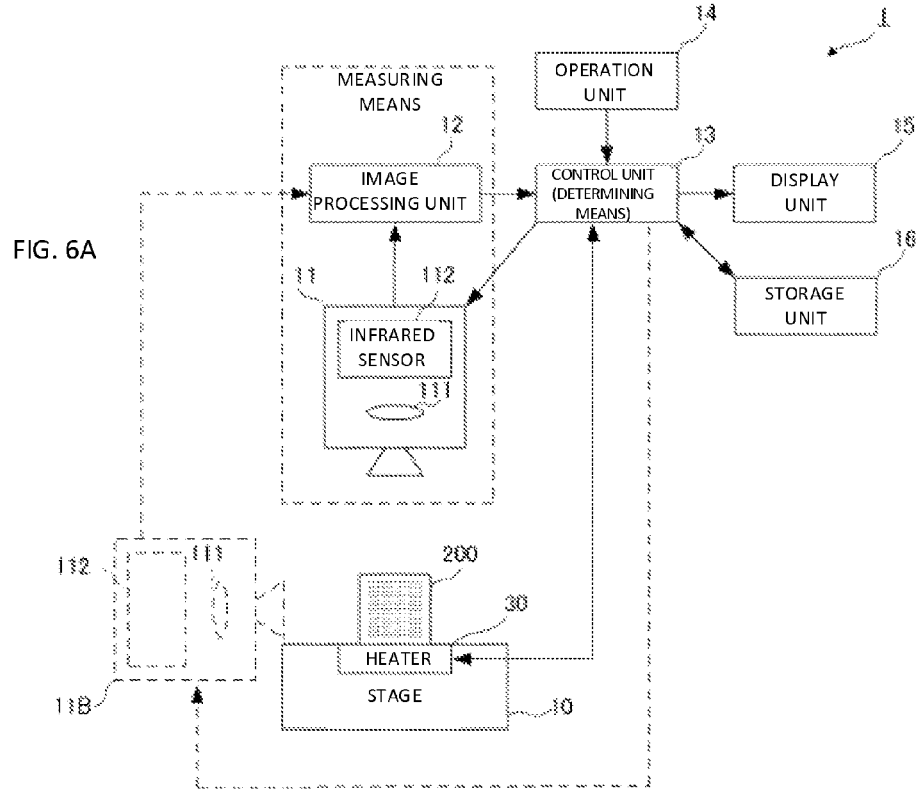
FIG. 6(A) is a block diagram of a layer direction determining apparatus for a multilayer electronic component according to a first embodiment of the present disclosure and FIG. 6(B) illustrates a capturing range of an infrared camera that captures an image of the observation face (the upper face) of a multilayer capacitor.
Figure 6B:
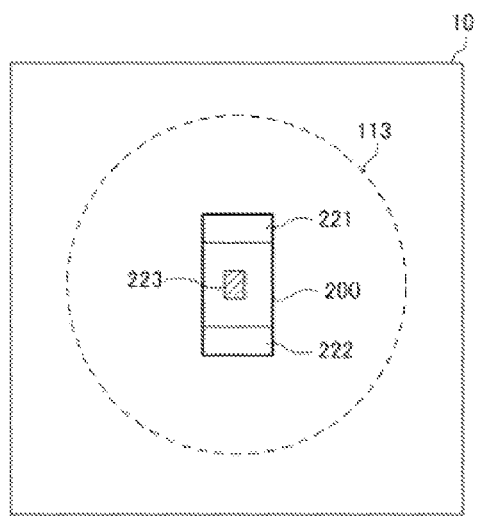

A layer direction determining apparatus for a multilayer electronic component according to a first embodiment of the present disclosure will now be described. FIG. 6(A) is a block diagram of the layer direction determining apparatus for a multilayer electronic component according to the first embodiment of the present disclosure. FIG. 6(B) illustrates a capturing range of the infrared camera that captures an image of the observation face (the upper face) of a multilayer capacitor.

As illustrated in FIG. 6(A), a layer direction determining apparatus 1 includes the stage 10, the infrared camera 11, an image processing unit 12, a control unit 13, an operation unit 14, a display unit 15, a storage unit 16, and the heater 30. The infrared camera 11 and the image processing unit 12 correspond to measuring means. The control unit 13 corresponds to determining means.

The infrared camera 11 includes an infrared ray supporting lens 111 and an infrared sensor 112. The infrared ray supporting lens 111 condenses an infrared ray that is incident on the infrared camera 11 on the infrared sensor 112. The infrared sensor 112 is an imaging element that captures an infrared thermal image corresponding to the amount of infrared energy detected from an object. The infrared sensor 112 has high sensitivity to the wavelengths from middle infrared rays to far infrared rays, that is, wavelengths from 1.5 μm to 16 μm. The infrared camera 11 captures the infrared thermal image corresponding to the infrared energy detected from the observation face (for example, the upper face) of the multilayer capacitor 200 placed on the heater 30 provided in an upper portion of the stage 10 to supply the infrared thermal image to the image processing unit 12.

The image processing unit 12 performs image processing to the thermal image supplied from the infrared camera 11 to convert the thermal image into different images so that a case in which the infrared energy detected from the multilayer capacitor 200 is higher than or equal to a threshold value is discriminated from a case in which the infrared energy detected from the multilayer capacitor 200 is lower than the threshold value. For example, the color of the image is varied depending on the infrared energy detected from the observation face of the multilayer capacitor 200.

The amount of infrared energy detected from the observation face of the multilayer capacitor 200 is varied with, for example, the ambient temperature, whether the multilayer capacitor 200 is heated, and/or the surface temperature of the heater 30. Accordingly, before the layer direction of the multilayer capacitor 200 is determined, the amounts of infrared energy detected from the parallel face and the perpendicular face of a reference multilayer capacitor are practically measured. The reference multilayer capacitor is a reference multilayer electronic component the shape and the characteristics of which are the same as those of the multilayer capacitor 200, which is a multilayer electronic component to be measured, and the layer direction of the conductor layers in which is known. The threshold value is set on the basis of the result of the measurement. In this case, the amounts of infrared energy detected from the parallel face and the perpendicular face may be used as the threshold values without processing. Specifically, the amount of infrared energy on the observation face of the reference multilayer capacitor is compared with the amount of infrared energy on the observation face of the multilayer capacitor 200 to be measured. Then, the magnitude relationship between the amount of infrared energy on the observation face of the reference multilayer capacitor and the amount of infrared energy on the observation face of the multilayer capacitor 200 is confirmed to accurately determine the layer direction of the conductor layers 205.

For example, when the observation face of the reference multilayer capacitor is the perpendicular face and the heater 30 is turned off, it is determined that the observation face of the multilayer capacitor 200 is the parallel face if (the amount of infrared energy on the observation face of the multilayer capacitor 200 to be measured)−(the amount of infrared energy on the observation face of the reference multilayer capacitor)>0. It is determined that the observation face of the multilayer capacitor 200 is the perpendicular face if (the amount of infrared energy on the observation face of the multilayer capacitor 200 to be measured)−(the amount of infrared energy on the observation face of the reference multilayer capacitor)≅0.

The threshold value may be set to a value, for example, an intermediate value between the measured value of the amount of infrared energy detected from the parallel face and the measured value of the amount of infrared energy detected from the perpendicular face.

The control unit 13 determines the layer direction of the multilayer capacitor on the basis of the image subjected to the image processing in the image processing unit 12. For example, when the heater 30 is turned off, the control unit 13 determines that the upper face of the multilayer capacitor 200 is parallel to the conductor layers if the infrared energy of the image is higher than or equal to the threshold value that is set in advance. The control unit 13 determines that the upper face of the multilayer capacitor 200 is perpendicular to the conductor layers if the infrared energy of the image is lower than the threshold value. The control unit 13 supplies the result of the determination of the layer direction of the multilayer capacitor 200 to the display unit 15.

The operation unit 14 accepts an operation to start or terminate the determination of the layer direction of the multilayer capacitor 200.

The display unit 15 displays, for example, the result of the determination of the layer direction of the multilayer capacitor 200.

The storage unit 16 stores programs executed by the control unit 13.

The heater 30 heats up the lower face of the multilayer capacitor 200. Turning on and off the heater 30 and the surface temperature of the heater 30 are controlled by the control unit 13. The heater 30 includes a temperature sensor (not illustrated). The surface temperature of the heater 30 is set to an arbitrary value, for example, not higher than 100° C. on the basis of a signal output from the temperature sensor.

Figure 7:
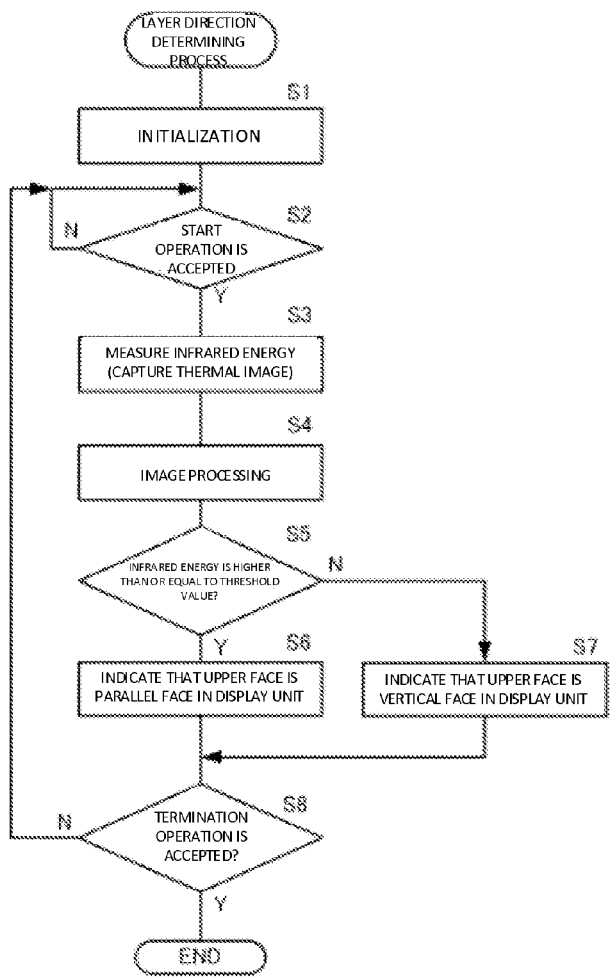
FIG. 7 is a flowchart for describing a layer direction determining process in the layer direction determining apparatus illustrated in FIG. 6(A).

A layer direction determining method performed by the layer direction determining apparatus 1 will now be described in detail with reference to a flowchart. FIG. 7 is a flowchart for describing a layer direction determining process in the layer direction determining apparatus for a multilayer electronic component illustrated in FIG. 6(A). Referring to FIG. 7, upon turning on of the layer direction determining apparatus 1, the control unit 13 performs an initialization process to confirm, for example, turning on or off of the heater 30 and the surface temperature when the heater 30 is turned on as the measurement conditions set in advance. The control unit 13 reads out a program from the storage unit 16 in accordance with the measurement conditions to execute the program (S1). The threshold value for determining the parallel face and the perpendicular face of the multilayer capacitor 200, which corresponds to the type of the multilayer capacitor 200 and the measurement conditions, is read out in the initialization process. When the type of the multilayer capacitor 200 to be measured is fixed, it is not necessary to read out the threshold value corresponding to the type.

The control unit 13 waits for an operation with the operation unit 14 (S2: N). If the control unit 13 acquires acceptance of an operation to start the layer direction determining process in the multilayer capacitor 200 with the operation unit 14 (S2: Y), the control unit 13 causes the infrared camera 11 to measure the amount of infrared energy detected from the upper face, which is the observation face, of the multilayer capacitor 200. Specifically, the control unit 13 causes the infrared camera 11 to capture a thermal image of the upper face of the multilayer capacitor 200 (S3). Step S3 corresponds to a capturing step. An area (a first area) where the infrared energy is measured is an area excluding the outer electrodes when the multilayer capacitor 200 is observed from above the upper face, as illustrated in FIG. 6(B). The size of the area where the measurement is performed may be a partial area in the area excluding the outer electrodes. For example, it is sufficient for the size of the area to be greater than the space between at least two conductor layers, as in an area 223 illustrated in FIG. 6(B).

The infrared camera 11 supplies the captured thermal image of the multilayer capacitor 200 to the image processing unit 12. The image processing unit 12 performs the image processing to the thermal image supplied from the infrared camera 11 so that the case in which the infrared energy detected from the multilayer capacitor 200 is higher than or equal to the threshold value is discriminated from the case in which the infrared energy detected from the multilayer capacitor 200 is lower than the threshold value. The image processing unit 12 supplies the image subjected to the image processing to the control unit 13 (S4). An averaging process may be performed on the thermal image. This allows the layer direction of the multilayer electronic component to be accurately determined even if the infrared energy detected from the observation face is slightly varied. Step S4 corresponds to a step of acquiring the measured value concerning the amount of infrared energy detected from the observation face. Steps S3 to S4 correspond to a measuring process.

If the infrared energy detected from the multilayer capacitor 200 is higher than or equal to the threshold value in the image supplied from the image processing unit 12 (S5: Y), the control unit 13 determines that the upper face of the multilayer capacitor 200 is parallel to the conductor layers. The control unit 13 indicates that the upper face of the multilayer capacitor 200 is parallel to the conductor layers in the display unit 15 (S6). If the infrared energy detected from the multilayer capacitor 200 is lower than the threshold value (S5: N), the control unit 13 determines that the upper face of the multilayer capacitor 200 is perpendicular to the conductor layers. The control unit 13 indicates that the upper face of the multilayer capacitor 200 is perpendicular to the conductor layers in the display unit 15 (S7). Step S5 corresponds to a comparing step. Steps S6 and S7 correspond to a step of determining that the observation face opposes the end portions of the conductor layers. Steps S5 to S7 correspond to a determining process. Since the magnitude relationship between the infrared energy and the threshold value and the positional relationship (parallel or perpendicular) of the conductor layers with respect to the upper face of the multilayer capacitor 200 may be reversed depending on the measurement conditions, the determination is performed in accordance with the magnitude relationship and the positional relationship that are reversed.

Steps S2 to S7 are repeated until the control unit 13 acquires acceptance of an operation to terminate the layer direction determining process in the multilayer capacitor 200 with the operation unit 14 (S8: N).

If the control unit 13 acquires acceptance of the operation to terminate the layer direction determining process in the multilayer capacitor 200 with the operation unit 14 (S8: Y), the layer direction determining process is terminated.

As described above, in the layer direction determining apparatus of the present disclosure, it is possible to accurately determine the layer direction of the conductor layers in the multilayer capacitor without destroying the multilayer capacitor. Since the determination can be performed in the state in which the multilayer capacitor is fixed, it is possible to determine the layer direction of the multilayer capacitor without damaging the multilayer capacitor.

The layer direction determining apparatus 1 may have a configuration in which the layer direction determining apparatus 1 further includes an infrared camera 11B indicated by a broken line in FIG. 6(A). The infrared camera 11 and the infrared camera 11B measure the infrared energies detected from the two adjacent faces with a longitudinal side of the multilayer capacitor having the rectangular parallelepiped shape sandwiched therebetween to supply the thermal images to the image processing unit 12. The image processing unit 12 performs the image processing so that the magnitude relationship between the infrared energies detected from the two respective faces of the multilayer capacitor 200 is determined. For example, the image having higher infrared energy detected from one face of the multilayer capacitor 200 is converted into a white image and the image having lower infrared energy detected from the other face of the multilayer capacitor 200 is converted into a black image. Before the image processing, the amounts of infrared energy detected from the parallel face and the perpendicular face of the reference multilayer capacitor are practically measured to associate the magnitude relationship between the infrared energies on the above two faces with the positional relationship of the conductor layers with respect to the upper face of the multilayer capacitor 200 in advance. The reference multilayer capacitor is a reference multilayer electronic component the shape and the characteristics of which are the same as those of the multilayer capacitor 200, which is a multilayer electronic component to be measured, and the layer direction of the conductor layers in which is known. The infrared energy measured with the infrared camera 11B is used as the threshold value and the infrared energy measured with the infrared camera 11 is compared with the threshold value to determine the positional relationship between the upper face of the multilayer capacitor 200, which opposes the infrared camera 11, and the conductor layers. The control unit 13 confirms and compares the two images subjected to the image processing in the image processing unit 12. When the heater 30 is turned off, the face having the higher infrared energy is determined to be parallel to the conductor layers. When the surface temperature of the heater 30 is set, for example, to 50° C., the face having the higher infrared energy is determined to be perpendicular to the conductor layers. The control unit 13 causes the display unit 15 to display the result of the determination.

In the comparison of the measured infrared energies on the two faces, the face having the higher infrared energy is determined to be parallel or perpendicular to the conductor layers depending on the turning on or off of the heater 30 and whether the surface temperature of the heater 30 is set in advance, which are the measurement conditions. Accordingly, the comparison between the measured infrared energies on the two faces allows the layer direction of the multilayer capacitor 200 to be determined.

Since the magnitude relationship between the infrared energies on the two faces and the positional relationship (parallel or perpendicular) of the conductor layers with respect to the upper face of the multilayer capacitor 200 may be reversed depending on the measurement conditions. Accordingly, for example, an experiment is performed in advance to set the threshold value corresponding to the measurement conditions and the determination is performed in accordance with the magnitude relationship and the positional relationship that are reversed.

One of the two adjacent faces with a longitudinal side of the multilayer capacitor 200 having the rectangular parallelepiped shape sandwiched therebetween is set as a first area and the other of the two adjacent faces is set as a second area. The difference between the measured values of the amounts of infrared energy detected from the first area and the second area may be compared with the threshold value to determine the layer direction of the conductor layers 205 in the multilayer capacitor 200. In this case, the threshold value is set in accordance with the measurement conditions and the type of the multilayer capacitor 200. The layer direction of the multilayer capacitor 200 can also be determined in this manner. Since the magnitude relationship between the infrared energy and the threshold value and the positional relationship (parallel or perpendicular) of the conductor layers with respect to the upper face of the multilayer capacitor 200 may be reversed depending on the measurement conditions, the determination is performed in accordance with the magnitude relationship and the positional relationship that are reversed.

In the layer direction determining apparatus 1, the layer direction of the multilayer capacitor 200 may be determined by performing the image processing in the image processing unit 12 on the basis of the thermal images captured by the infrared cameras 11 and 11B so that the display temperature on the observation face of the multilayer capacitor 200 is determined. As is well known in the art, the relationship between the detected infrared energy and the temperature can be calculated according to Stefan-Boltzmann's law and Planck's law. Accordingly, the layer direction determining apparatus 1 is configured so as to use these laws to output an image corresponding to the display temperature on the observation face of the multilayer capacitor 200 or to directly output the display temperature on the observation face of the multilayer capacitor 200. Since the temperature displayed on the parallel face of the multilayer capacitor 200 is different from the temperature displayed on the perpendicular face thereof, as described above, it is possible to compare the display temperature on the observation face of the multilayer capacitor 200 with the threshold value that is set in advance by the control unit 13 to determine the layer direction of the multilayer capacitor 200 on the basis of temperature information.

When the layer direction of the multilayer capacitor is determined on the basis of the display temperature, the threshold value is set to a value (for example, an intermediate value) between the display temperature of the parallel face of the multilayer capacitor and the display temperature of the perpendicular face thereof.

Instead of the calculation of the display temperature on the observation face from the infrared energy detected from the observation face of the multilayer capacitor in the above manner, the observation face of the multilayer capacitor may be directly measured with, for example, an infrared radiation thermometer to determine the layer direction of the multilayer capacitor.

Second Embodiment

Figure 8A:
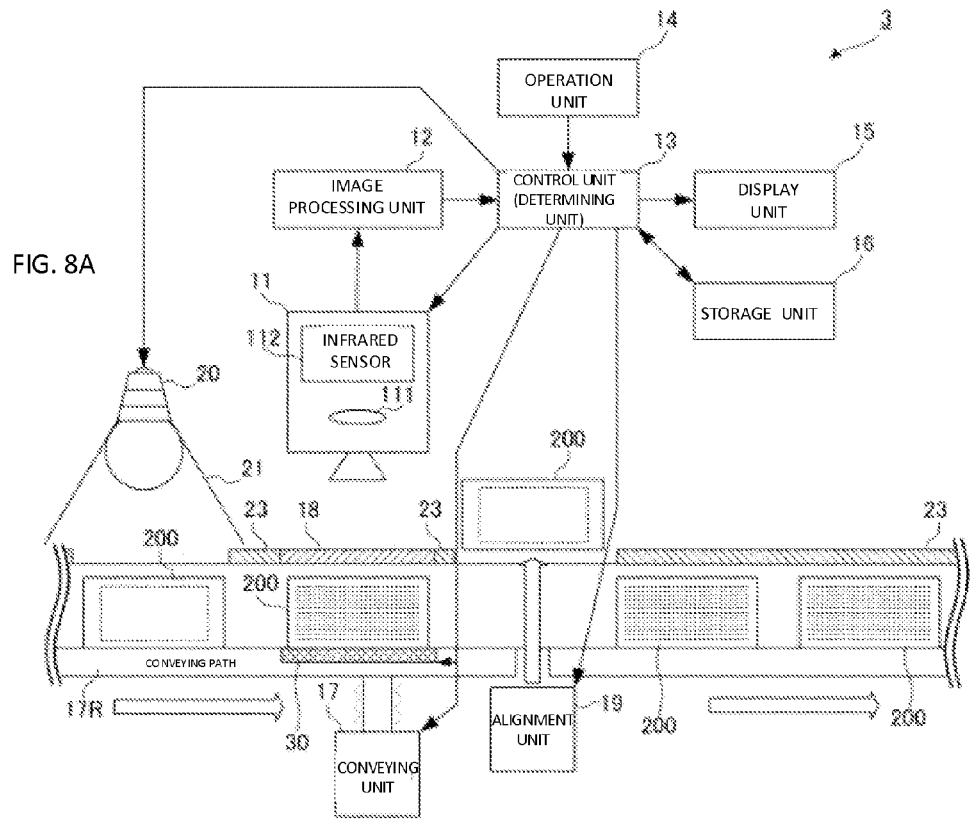
FIG. 8(A) is a block diagram of a layer direction determining apparatus for a multilayer electronic component according to a second embodiment of the present disclosure and FIG. 8(B) illustrates a capturing range of the infrared camera that captures an image of the observation face (the upper face) of a multilayer capacitor.
Figure 8B:
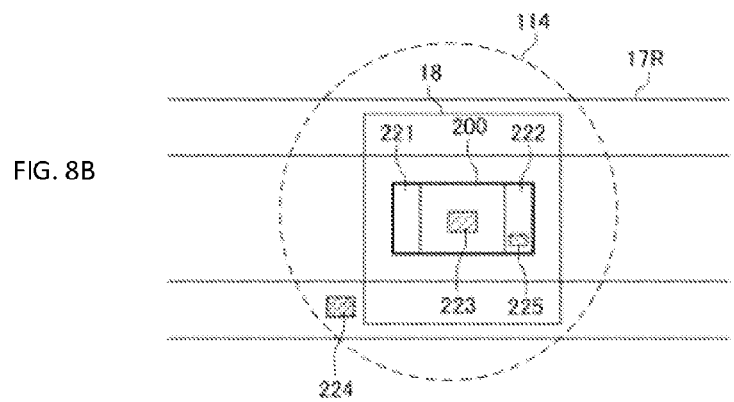
Figure 9:
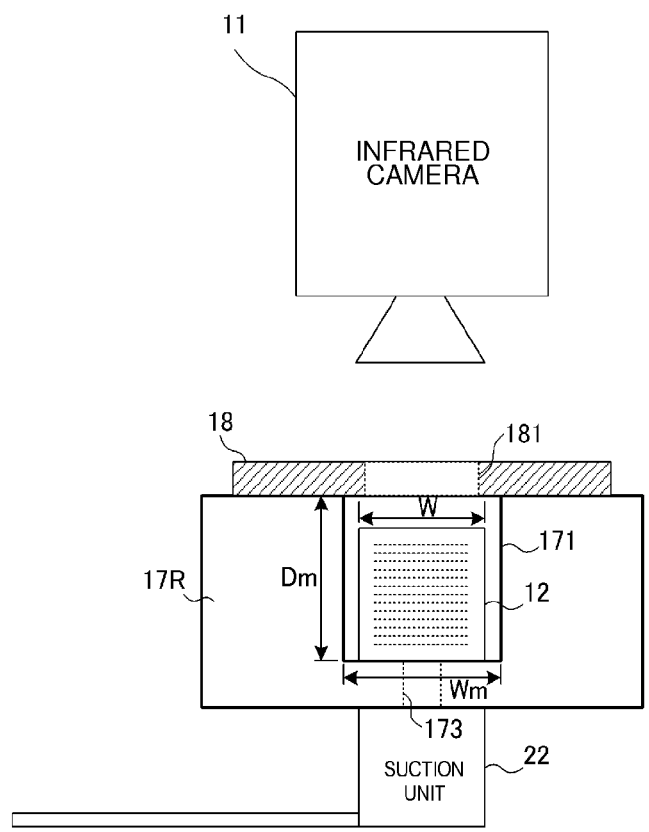
FIG. 9 is a cross-sectional view illustrating the structure of a conveying path.

A layer direction determining apparatus for a multilayer electronic component according to a second embodiment of the present disclosure will now be described. FIG. 8(A) is a block diagram of the layer direction determining apparatus for a multilayer electronic component according to the second embodiment of the present disclosure. FIG. 8(B) illustrates a capturing range of the infrared camera that captures an image of the observation face (the upper face) of a multilayer capacitor. FIG. 9 is a cross-sectional view illustrating the structure of a conveying path.

A layer direction determining apparatus 3 illustrated in FIG. 8(A) has a configuration in which a conveying unit 17 that conveys the multilayer capacitor 200 along a conveying path 17R and an alignment unit 19 that changes the orientation of each multilayer electronic component so that the layer direction is aligned with a certain layer direction are added to the configuration of the layer direction determining apparatus 1 illustrated in FIG. 6(A). The layer direction determining apparatus 3 may be referred to as a direction alignment apparatus because the layer direction determining apparatus 3 determines the layer direction of the multilayer electronic component and changes the orientation of the multilayer electronic component.

The conveying unit 17 illustrated in FIG. 8(A) gives vibration to the conveying path 17R, like a parts feeder, to move the multilayer capacitor 200. A groove 171 along which the multilayer capacitor 200 is conveyed is formed in an upper face side portion of a central part of the conveying path 17R, as illustrated in FIG. 9. The infrared camera 11 is provided above the groove 171 of the conveying path 17R. A cover 18 is provided between the conveying path 17R and the infrared camera 11, that is, over the groove 171 of the conveying path 17R. The cover 18 corresponds to a cover member. The cover 18 is fixed between the multilayer capacitor 200 and the infrared camera 11 in order to prevent the multilayer capacitor 200 from jumping out of the groove 171 of the conveying path 17R. A stainless cover 23 is provided in portions excluding the portions where the alignment unit 19 and the lamp 20 described below are provided, above the groove 171 of the conveying path 17R, in addition to the cover 18.

When the size of the multilayer capacitor 200 is 1.0 mm long×0.5 mm wide and has a height of 0.5 mm, the size of the groove formed in the conveying path 17R is set to, for example, 0.55 mm wide (Wm)×0.55 mm depth (Dm). In other words, the depth of the groove is made greater than the height of the multilayer capacitor 200 and the cover 18 is spaced out from the multilayer capacitor 200. The width of the groove is made greater than the width of the multilayer capacitor 200 to allow the multilayer capacitor 200 to be conveyed along the conveying path 17R. If the cover 18 comes into contact with the multilayer capacitor 200, heat conduction is dominant over radiation in heat propagation and it is difficult to measure the infrared energy detected from the multilayer capacitor 200. However, in the above configuration, the cover 18 is normally not in contact with the multilayer capacitor 200 and the multilayer capacitor 200 comes into contact with the cover 18 only when the multilayer capacitor 200 jumps up due to the vibration. Accordingly, it is possible to measure the infrared energy detected from the multilayer capacitor 200 with no problem.

The cover 18 is preferably made of a material having transmission characteristics for the infrared rays. For example, the cover 18 is preferably made of Ge (germanium) having an infrared transmittance of 90% or higher, ZnS (zinc sulfide) having an infrared transmittance of 70% or higher, or Ge—Sb—Se (chalcogenide glass) having an infrared transmittance of 65% or higher. For example, when Ge is used, the thickness of the cover 18 is set to about 2 mm.

A face of the cover 18 at the infrared camera 11 side is subjected to anti-reflection (AR) coating. The coating prevents an image captured by the infrared camera 11 from being affected by reflected light.

A face of the cover 18 at the multilayer capacitor 200 side is subjected to diamond like carbon (DLC) coating to form a protective surface film. The protective surface film prevents the cover 18 from being worn or scratched even if the multilayer capacitor 200 jumps up due to the vibration during the conveyance of the multilayer capacitor 200.

A through hole 181 smaller than the width W, which corresponds to the short sides of the multilayer capacitor 200, may be provided in the cover 18. In this case, an image of the upper face of the multilayer capacitor 200 is captured by the infrared camera 11 only via the through hole 181 or via the cover 18 and the through hole 181. The provision of the through hole 181 in the cover 18 allows the infrared energy detected from the multilayer capacitor 200 via the through hole 181 to be measured with no problem even if the multilayer capacitor 200 conveyed along the groove of the conveying path 17R abuts against the cover 18 to damage the cover 18.

When the through hole 181 is provided in the cover 18 in the above manner, a material, such as stainless steel (SUS), through which the infrared rays are not transmitted may be used.

The through hole 181 provided in the cover 18 is made smaller than the width W of the multilayer capacitor 200 in order to prevent the multilayer capacitor 200 that jumps out of the groove 171 due to the vibration from being fitted into the through hole 181.

Although the multilayer capacitor 200 vibrates while the multilayer capacitor 200 is being conveyed along the conveying path 17R, temporary stop of the conveyance of the multilayer capacitor 200 when an image of the multilayer capacitor 200 is captured allows the effect of the vibration to be suppressed. As a configuration to temporarily stop the conveyance of the multilayer capacitor 200, a configuration in which the multilayer capacitor 200 is magnetically fixed or fixed by suction is preferably used. For example, as illustrated in FIG. 9, a through hole 173 is provided in a bottom part of the groove 171 and a suction unit 22 is provided below the groove 171 to fix the multilayer capacitor 200 by suction at an end portion of the through hole 173. This allows an image of the multilayer capacitor 200 to be captured without stopping the conveying unit 17.

The alignment unit 19 illustrated in FIG. 8(A) changes the orientation of the multilayer capacitor 200 so that the layer direction is aligned in a certain direction on the basis of the result of the determination of the layer direction of the multilayer capacitor 200 by the control unit 13.

A discharge unit may be used for the alignment unit 19. The discharge unit discharges the multilayer capacitor 200 the determined layer direction of which is different from the specific direction from the conveying path 17R and leaves the multilayer capacitor 200 the determined layer direction of which is the specific direction. In this case, the multilayer capacitor 200 is discharged from the conveying path 17R by using air or magnetic force.

A direction changing unit may be used for the alignment unit 19. The direction changing unit changes the orientation of the multilayer capacitor 200 the determined layer direction of which is different from the specific direction to align the layer directions of the multilayer capacitors 200 that are conveyed in the specific direction. In this case, a rotation mechanism is provided to rotate the multilayer capacitor 200 in order to change the orientation.

In the layer direction determining apparatus 3, the lamp 20, which is a heating means for the multilayer capacitor 200, may be provided and the layer direction may be determined after the multilayer capacitor 200 is heated with the lamp 20 to set the multilayer capacitor 200 to a temperature state higher than the normal temperature. The heating of the multilayer capacitor 200 increases the infrared energy detected from the observation face of the multilayer capacitor 200. Accordingly, the difference between the infrared energy detected from the parallel face with respect to the conductor layers in the multilayer capacitor 200 and that detected from the perpendicular face with respect to the conductor layers in the multilayer capacitor 200 is increased to facilitate the determination of the layer direction of the multilayer capacitor.

In order to heat the multilayer capacitor 200, for example, a method of irradiating the multilayer capacitor 200 with visible light or infrared rays with the lamp 20 illustrated in FIG. 8(A), a method of irradiating the multilayer capacitor 200 with laser light having a waveform similar to that of the infrared rays measured by the infrared camera, or an induction heating method is used.

Instead of the lamp 20, the heater 30 may be used as in FIG. 6(A). Specifically, the heater 30 is provided at a position where the temperature of the multilayer capacitor 200 is measured with the infrared camera 11, without turning on the lamp 20 in the manner illustrated in FIG. 8(A), and the surface temperature of the heater 30 is set to a high value (for example, a value from 50° C. to 100° C.) This also increases the difference between the infrared energy detected from the parallel face with respect to the conductor layers in the multilayer capacitor 200 and that detected from the perpendicular face with respect to the conductor layers in the multilayer capacitor 200 to facilitate the determination of the layer direction of the multilayer capacitor.

When the multilayer capacitors 200 are heated by the above methods, the multilayer capacitors 200 are controlled so that the same amount of energy is applied to the multiple multilayer capacitors 200. This control prevents an occurrence of a problem in that the infrared energies detected from the multilayer capacitors 200 are varied.

In the configuration illustrated in FIG. 8(A), the multilayer capacitor 200 is conveyed along the conveying path 17R at a substantially constant speed by the conveying unit 17. A lampshade 21 is mounted to the lamp 20 in order to limit the range to be irradiated with the light to a certain range. Accordingly, the amount of energy applied to the multilayer capacitor 200 is made substantially constant in a state in which the light intensity of the lamp 20 is constant.

The lamp 20 that heats up the multilayer capacitor 200 may also be provided in the layer direction determining apparatus 1 illustrated in FIG. 6(A).

In the layer direction determining apparatus 3, the two infrared cameras may be provided, as in the layer direction determining apparatus 1 illustrated in FIG. 6(A), to measure the infrared energies detected from the two respective adjacent faces with a longitudinal side of the multilayer capacitor 200 sandwiched therebetween. When the lamp 20, which is the heating means for the lamp 20, is provided in this configuration, the lamp 20 is arranged so that the same amount of energy is applied to the two adjacent faces of the multilayer capacitor 200. This allows the layer direction of the multilayer capacitor 200 to be accurately determined.

Alternatively, the measured values of the amounts of infrared energy detected from a first area and a second area other than the first area may be acquired and the layer direction of the multilayer capacitor may be determined on the basis of the difference between the measured value of a first amount of infrared energy and the measured value of a second amount of infrared energy.

For example, when the temperature of the multilayer capacitor is greatly varied due to the change in ambient temperature, the layer direction of the multilayer capacitor may not be accurately determined with the threshold value that is initially set. In such a case, since the temperature of a member around the multilayer capacitor is also varied in the same manner as in the multilayer capacitor, the variation in temperature of the member around the multilayer capacitor is used. Specifically, the area where the measured value of the amount of infrared energy of the multilayer capacitor is measured is set as the first area. The measured value of the amount of infrared energy detected from the second area other than the multilayer capacitor is acquired. Then, the difference between the measured value of the amount of infrared energy detected from the second area, which is used as a reference value, and the measured value of the amount of infrared energy detected from the first area is calculated to acquire a relative value of the measured value of the amount of infrared energy. This allows the variation in temperature in the multilayer capacitor itself to be supported. Similarly, also when the sensitivity of the infrared camera is varied with the variation in ambient temperature, it is possible to accurately determine the layer direction of the multilayer capacitor by acquiring the relative value of the measured value of the amount of infrared energy.

For example, as illustrated in FIG. 8(B), the area 223, which is a partial area of the area excluding the outer electrodes in the multilayer capacitor 200, is set as the first area and the measured value of the first amount of infrared energy is acquired from the first area. An area other than the multilayer capacitor, such as a partial area 224 on the conveying path 17R within a field of view 114 of the infrared camera 11, is set as the second area and the measured value of the second amount of infrared energy is acquired from the second area. Then, the difference (the relative value) between the measured value of the first amount of infrared energy and the measured value of the second amount of infrared energy is calculated to compare the relative value with the threshold value that is set in advance.

When the amount of infrared energy is varied depending on the orientation of the multilayer capacitor in the first area, the area other than the observation face of the multilayer capacitor, in which the measured value of the amount of infrared energy is not varied regardless of the orientation of the multilayer electronic component, may be set as the second area and the measured value of the amount of infrared energy may be acquired from the second area. Specifically, a partial area 225 on the outer electrode illustrated in FIG. 8(B) or an area (not illustrated) on a side face of the body (a side margin) of the multilayer electronic component is set as the second area and the measured value of the amount of infrared energy is acquired from the second area.

The above methods allow the layer direction of the multilayer capacitor to be accurately determined even if the temperature of the multilayer capacitor is greatly varied with the variation in ambient temperature.

Figure 10:
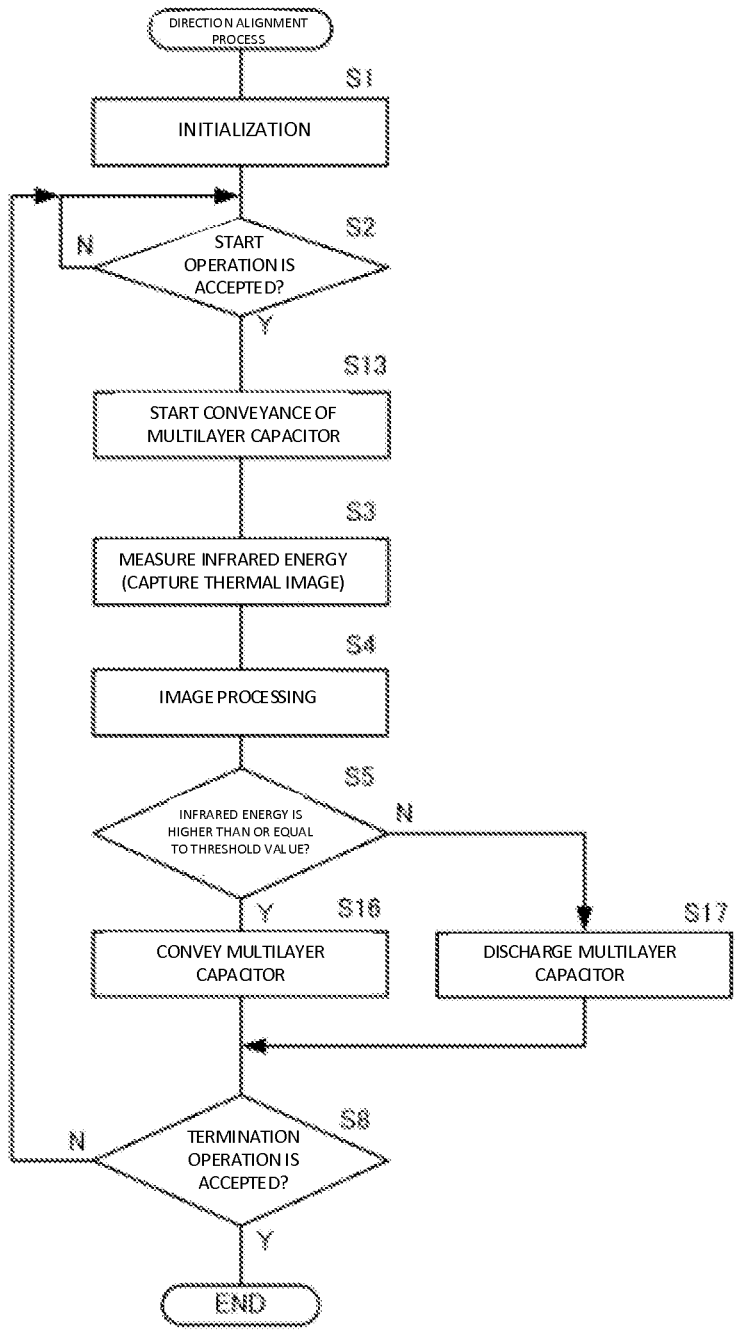
FIG. 10 is a flowchart for describing a direction alignment process in the layer direction determining apparatus illustrated in FIG. 8(A).

A layer direction determining method performed by the layer direction determining apparatus 3 will now be described in detail with reference to a flowchart. FIG. 10 is a flowchart for describing a direction alignment process in the layer direction determining apparatus for a multilayer electronic component illustrated in FIG. 8. The same reference numerals are used in FIG. 10 to identify the same steps illustrated in FIG. 7. Steps that are not included in the flowchart illustrated in FIG. 7 are mainly described in the following description.

Referring to FIG. 10, upon turning on of the layer direction determining apparatus 3, the control unit 13 performs the processing in Step S1. In Step S1, the control unit 13 confirms, for example, turning on or off of either of the lamp 20 and the heater 30 and the surface temperature when the heater 30 is turned on as the measurement conditions set in advance. The control unit 13 reads out a program from the storage unit 16 in accordance with the measurement conditions to execute the program. The threshold value for determining the parallel face and the perpendicular face of the multilayer capacitor 200, which corresponds to the type of the multilayer capacitor 200 and the measurement conditions, is read out in the initialization process. When the type of the multilayer capacitor 200 to be measured is fixed, it is not necessary to read out the threshold value corresponding to the type.

The control unit 13 waits for an operation with the operation unit 14 (S2: N). If the control unit 13 acquires acceptance of an operation to start the direction alignment process in the multilayer capacitor 200 with the operation unit 14 (S2: Y), the control unit 13 causes the conveying unit in the infrared camera 11 to start conveyance of the multilayer capacitor 200 along the conveying path 17R (S13). At this time, the multilayer capacitor 200 that is being conveyed is heated up by the lamp 20. Then, Steps S3 to S5 are performed. Step S13 corresponds to a conveying process and a process of heating up the multilayer electronic component.

If the infrared energy detected from the multilayer capacitor 200 is higher than or equal to the threshold value in the image supplied from the image processing unit 12 (S5: Y), the control unit 13 determines that the upper face of the multilayer capacitor 200 is parallel to the conductor layers. The control unit 13 conveys the multilayer capacitor 200 downstream (S16). If the infrared energy detected from the multilayer capacitor 200 is lower than the threshold value (S5: N), the control unit 13 determines that the upper face of the multilayer capacitor 200 is perpendicular to the conductor layers. Since the magnitude relationship between the infrared energy and the threshold value and the positional relationship (parallel or perpendicular) of the conductor layers with respect to the upper face of the multilayer capacitor 200 may be reversed depending on the measurement conditions, the determination is performed in accordance with the magnitude relationship and the positional relationship that are reversed. The control unit 13 discharges the multilayer capacitor 200 from the conveying path 17R with the alignment unit 19 (S17). The multilayer capacitor 200 discharged from the conveying path 17R is returned upward along the conveying path 17R with a mechanism (not illustrated) and a thermal image is captured again by the infrared camera 11. Steps S16 and S17 correspond to a process of changing the orientation of the multilayer electronic component so that the layer direction is aligned with a certain layer direction.

Steps S2 to S17 are repeated until the control unit acquires acceptance of an operation to terminate the direction alignment process in the multilayer capacitor 200 with the operation unit 14 (S8: N).

If the control unit 13 acquires acceptance of the operation to terminate the direction alignment process in the multilayer capacitor 200 with the operation unit 14 (S8: Y), the direction sorting process is terminated.

Figure 11A:
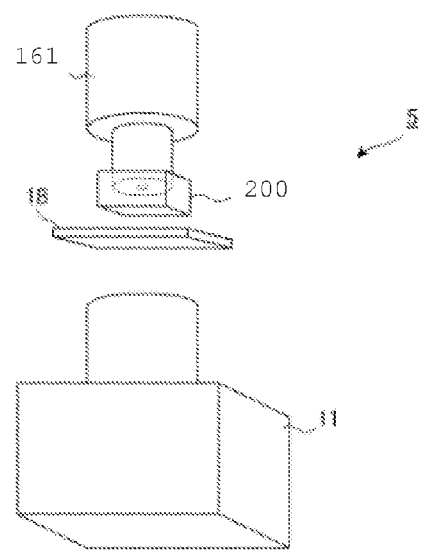
FIG. 11(A) schematically illustrates a suction nozzle in an assembling machine to which the layer direction determining apparatus is applied and FIG. 11(B) schematically illustrates a taping machine to which the layer direction determining apparatus is applied.
Figure 11B:
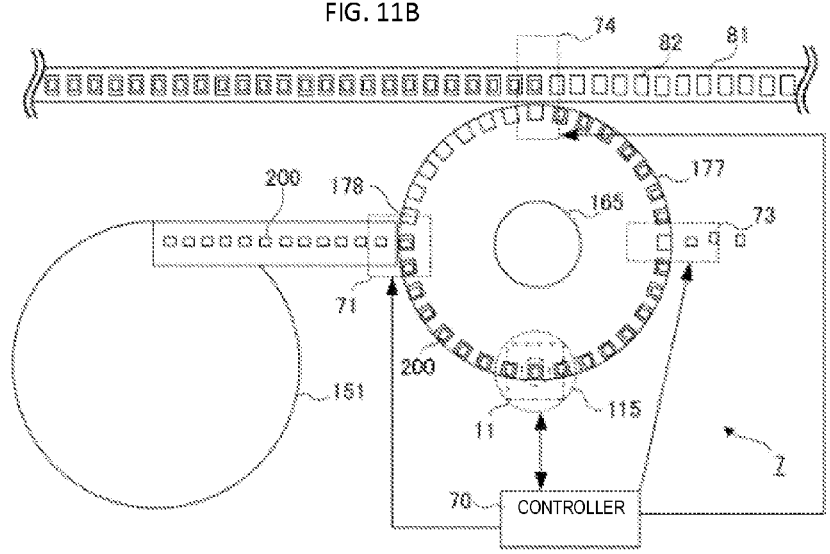

As described above, in the layer direction determining apparatus 3 of the present disclosure, it is possible to accurately determine the layer direction of the multilayer capacitor to align the layer directions. Other configurations of layer direction determining apparatus FIG. 11(A) schematically illustrates a suction nozzle in an assembling machine to which the layer direction determining apparatus is applied. FIG. 11(B) schematically illustrates a taping machine to which the layer direction determining apparatus is applied.

The configuration of the layer direction determining apparatus 3 is not limited to the one illustrated in FIG. 8(A) and may be configured in the following manner. For example, the configuration of the layer direction determining apparatus is applicable to an assembling machine or a component mounting machine. Specifically, in an assembling machine 5, a suction nozzle 161 illustrated in FIG. 11(A) and a moving mechanism (not illustrated) that moves the suction nozzle 161 corresponds to the conveying unit 17 and the alignment unit 19 in the layer direction determining apparatus 3.

In the assembling machine 5, the layer directions of the multilayer capacitors are aligned in the following manner. First, the multilayer capacitor 200 in a component tray (not illustrated) is adsorbed and held with the suction nozzle 161. The suction nozzle 161 is moved in the air, which is the conveying path, to the location where the infrared camera 11 is provided. An image of the bottom face of the multilayer capacitor 200 is captured with the infrared camera 11 in the state in which the multilayer capacitor 200 is adsorbed and held with the suction nozzle 161 to determine the direction. The cover 18 is provided between the suction nozzle and the infrared camera 11 in order to prevent the multilayer capacitor 200 from dropping down and abutting against the infrared camera 11. If the determination indicates that the multilayer capacitor 200 has a desired layer direction (for example, the bottom face side is parallel to the conductor layers), the multilayer capacitor 200 is conveyed to a next assembly process. If the determination indicates that the multilayer capacitor 200 has a layer direction different from the desired layer direction (for example, the bottom face side is perpendicular to the conductor layers), for example, the multilayer capacitor 200 is dropped so as to change the orientation of the multilayer capacitor 200 and is returned to the component tray.

Method and Apparatus of Manufacturing a Series of Multilayer Electronic Components The configuration of the layer direction determining apparatus 3 is applicable to a taping machine, which is an apparatus of manufacturing a series of multilayer electronic components. Specifically, in a taping machine 7, a rotary circular plate 177 illustrated in FIG. 11(B) corresponds to the conveying path. A rotating mechanism (motor) 165 that rotates the rotary circular plate 177 corresponds to the conveying unit 17. Air outlets and blow-off units (not illustrated) provided in cavities of the rotary circular plate 177 correspond to the alignment unit 19.

Figure 12:
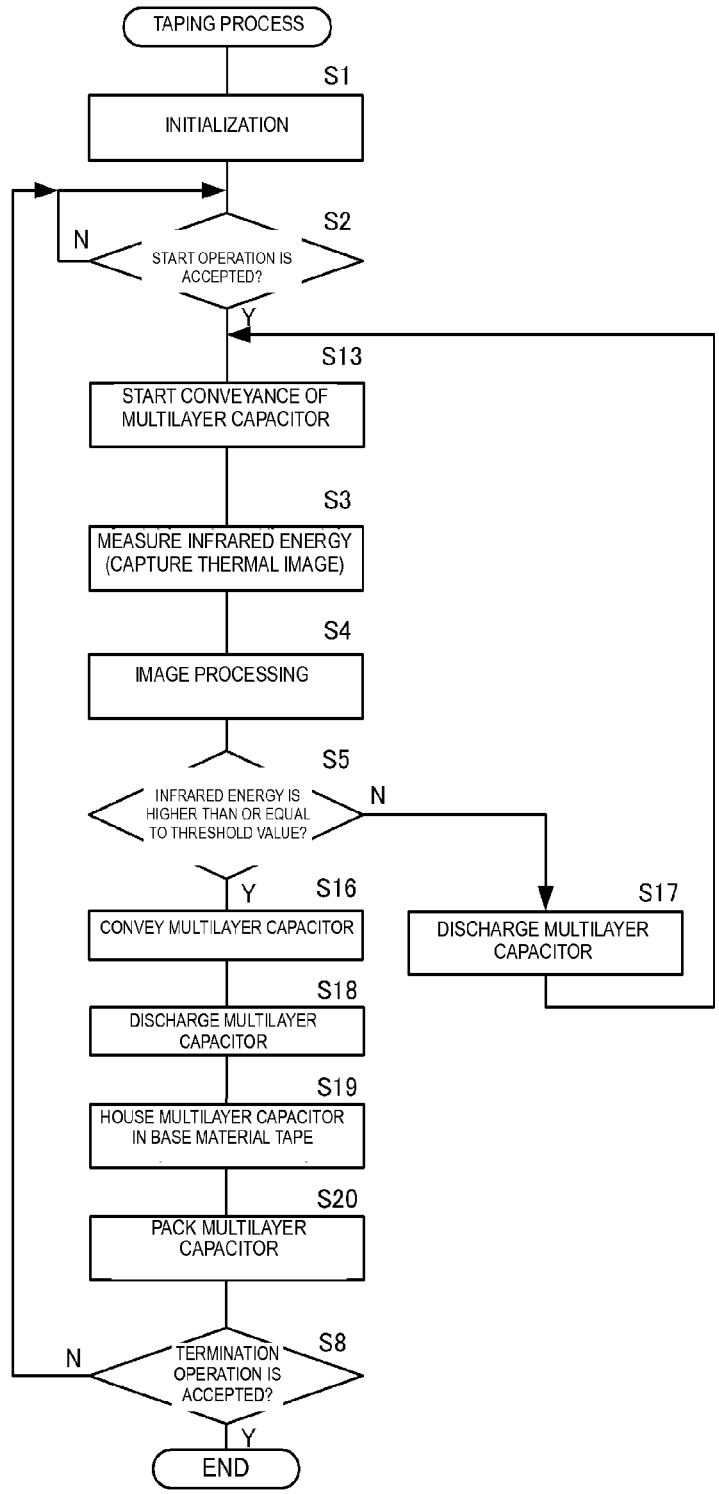
FIG. 12 is a flowchart for describing a process of manufacturing a series of multilayer electronic components in the taping machine illustrated in FIG. 11(B).

FIG. 12 is a flowchart for describing a process of manufacturing a series of multilayer electronic components in the taping machine illustrated in FIG. 11(B). The same reference numerals are used in FIG. 12 to identify the same steps illustrated in FIG. 10. Steps that are not included in the flowchart illustrated in FIG. 10 are mainly described in the following description.

In the taping machine 7, for example, the layer directions of the multilayer capacitors are aligned in the following manner. A controller 70 in the taping machine 7 puts the multilayer capacitor 200 conveyed from a component tray 151 into a cavity 178 of the rotary circular plate 177 in an insertion area 71 (S13). The rotating mechanism 165 rotates the rotary circular plate 177 at a certain speed to move the multilayer capacitor 200 to an image capturing area 115 of the infrared camera 11 (S13). The infrared camera 11 captures an image of the upper face of the multilayer capacitor 200 and the controller 70 determines its layer direction. Specifically, a thermal image is captured (S3), the image processing is performed (S4), and the infrared energy is compared with the threshold value (S5). In the image capturing area 115, the infrared camera 11 is provided at the upper face side of the rotary circular plate 177.

If the determination indicates that the multilayer capacitor 200 has a desired layer direction (for example, the upper face side is parallel to the conductor layers), upon movement of the multilayer capacitor 200 the layer direction of which is determined with respect to a housing area (S16), the controller 70 causes the air outlet in a housing unit 74 to blow off the air to discharge the multilayer capacitor 200 (S18). The controller 70 houses the multilayer capacitors 200 in housings 82 of a base material tape 81 conveyed by a taping unit (not illustrated) one by one in a state in which the layer directions of the multilayer capacitors 200 are aligned with the certain layer direction (S19). The base material tape is conveyed downward and a cover tape is bonded to the upper face of each multilayer capacitor 200 to pack the multilayer capacitor 200 (S20). If the determination indicates that the multilayer capacitor 200 has a layer direction different from the desired layer direction (for example, the upper face side is an end face), upon movement of the multilayer capacitor 200 the layer direction of which is determined with respect to a sorting area at the near side of the housing area, the controller 70 causes the air outlet in a sorting unit 73 to blow off the air to discharge the multilayer capacitor 200 (S17). The multilayer capacitor 200 discharged in the sorting unit 73 is housed in the component tray 151 with a conveying mechanism (not illustrated) to be subjected to a sorting process based on the layer direction of the conductor layers and a housing process again. The series of multilayer electronic components in which the conductor layers are aligned with the certain layer direction are manufactured in the above manner.

Steps S5, S16, and S17 correspond to the sorting process. Step S19 corresponds to the housing process.

The layer direction determining apparatus for a multilayer electronic component of the present disclosure is also capable of determining the layer direction of a multilayer electronic component in a state in which the multilayer electronic component is mounted on a printed circuit board. Specifically, it is possible to determine the layer direction of the multilayer electronic component by capturing an image of the multilayer electronic component on the printed circuit board with the infrared camera without being affected by other electronic components mounted around the multilayer electronic component on the printed circuit board and the printed circuit board positioned at the rear face side of the multilayer electronic component.

INDUSTRIAL APPLICABILITY

The present disclosure is applicable to a determination apparatus for determining the layer direction of the conductor layers in a multilayer electronic component and an apparatus for manufacturing a series of multilayer electronic components to align the layer directions of the conductor layers in the multilayer electronic components in a certain direction.

The invention claimed is:

1. A layer direction determining method for a multilayer electronic component, the layer direction determining method comprising:
    measuring a value of an amount of infrared energy detected from an area including an observation face where a multilayer electronic component in which conductor layers and nonconductor layers are layered is observed under a measurement condition that is set in advance;
    determining a threshold value corresponding to the measurement condition;
    comparing the threshold value with the measured value of the detected amount of infrared energy; and
    determining a layer direction of the conductor layers in the multilayer electronic component on the basis of the result of the comparison of the threshold value with the measured value of the detected amount of infrared energy.

2. The layer direction determining method for a multilayer electronic component according to claim 1,
    wherein the measured value is a difference between detected values detected from a first area on the observation face and a second area different from the first area.

3. The layer direction determining method for a multilayer electronic component according to claim 2,
    wherein the first area is one of two adjacent faces with a longitudinal side of the multilayer electronic component having a rectangular parallelepiped shape sandwiched therebetween, and
    wherein the second area is the other of the two adjacent faces.

4. The layer direction determining method for a multilayer electronic component according to claim 2,
    wherein the first area is an area excluding an outer electrode of the multilayer electronic component, and
    wherein the second area is an area other than the multilayer electronic component.

5. The layer direction determining method for a multilayer electronic component according to claim 2,
    wherein the first area is an area where the amount of infrared energy is varied depending on an orientation of the multilayer electronic component, and
    wherein the second area is an area on the multilayer electronic component where the amount of infrared energy is constant regardless of the orientation of the multilayer electronic component.

6. The layer direction determining method for a multilayer electronic component according to claim 1,
    wherein the measurement condition includes at least one of the presence of heating of the multilayer electronic component, a heating direction, and a heating temperature.

7. The layer direction determining method for a multilayer electronic component according to claim 1,
    wherein the threshold value is set on a basis of a measured value concerning an amount of infrared energy detected from an observation face of a reference multilayer electronic component a shape and characteristics of which are the same as those of the multilayer electronic component to be measured and the layer direction of the conductor layers is known when the reference multilayer electronic component is measured under the measurement condition.

8. The layer direction determining method for a multilayer electronic component according to claim 1,
    wherein the multilayer electronic component in the measuring step is in a temperature state higher than normal temperature.

9. The layer direction determining method for a multilayer electronic component according to claim 1,
    wherein the measuring step includes
        capturing a thermal image on the observation face of the multilayer electronic component; and
        acquiring the measured value on a basis of the thermal image captured in the capturing step.

10. The layer direction determining method for a multilayer electronic component according to claim 1,
wherein the measured value is a temperature.

11. A method of manufacturing a series of multilayer electronic components housed in a base material including a plurality of housings, the method comprising:
sorting a plurality of multilayer electronic components the conductor layers in which are determined to have a certain layer direction by measuring a value of an amount of infrared energy detected from an area including an observation face where a multilayer electronic component in which conductor layers and nonconductor layers are layered is observed under a measurement condition that is set in advance;
determining a threshold value corresponding to the measurement condition;
comparing the threshold value with the measured value of the detected amount of infrared energy;
determining a layer direction of the conductor layers in the multilayer electronic component on the basis of the result of the comparison of the threshold value with the measured value of the detected amount of infrared energy; and
housing the plurality of sorted multilayer electronic components in the plurality of housings in a state in which the conductor layers are aligned with the certain layer direction.

12. The method of manufacturing a series of multilayer electronic components according to claim 11, further comprising:
changing an orientation of the multilayer electronic component so that the layer direction is aligned in the certain layer direction when the layer direction of the conductor layers determined in the determining method is different from the certain layer direction.

* * * * *